US008080566B1

(12) United States Patent (10) Patent No.: US 8,080,566 B1
Kahraman et al. (45) Date of Patent: Dec. 20, 2011

(54) CARBAZOLE INHIBITORS OF HISTAMINE RECEPTORS FOR THE TREATMENT OF DISEASE

(75) Inventors: Mehmet Kahraman, San Diego, CA (US); Allen J. Borchardt, San Diego, CA (US); Robert L. Davis, Carlsbad, CA (US); Stewart A. Noble, San Diego, CA (US); James W. Malecha, San Diego, CA (US)

(73) Assignee: Kalypsys, Inc, Del Mar, CA (US)

( * ) Notice: Subject to any disclaimer, the term of this patent is extended or adjusted under 35 U.S.C. 154(b) by 0 days.

(21) Appl. No.: 12/482,989

(22) Filed: Jun. 11, 2009

Related U.S. Application Data

(60) Provisional application No. 61/060,622, filed on Jun. 11, 2008.

(51) Int. Cl.
*C07D 401/14* (2006.01)
*A61K 31/454* (2006.01)

(52) U.S. Cl. .......................................... 514/323; 546/200
(58) Field of Classification Search .................. 514/323; 546/200
See application file for complete search history.

(56) References Cited

FOREIGN PATENT DOCUMENTS

| WO | 9626927 | 9/1996 |
| WO | 0107409 | 2/2001 |
| WO | 02072570 | 9/2002 |
| WO | 2006074025 | 7/2006 |
| WO | 2008021745 | 2/2008 |
| WO | WO 2009136175 A1 * | 11/2009 |

OTHER PUBLICATIONS

U.S. Department of Health & Human Services Diseases and Conditions Index, Asthma (http://www.nhlbi.nih.gov/health/dci/Diseases/Asthma/Asthma_Prevention.html, accessed Jul. 14, 2010).*
WebMD, Allergies Health Center, Allergic Rhinitis (http://www.webmd.com/allergies/tc/allergic-rhinitis-prevention, accessed Jul. 14, 2010).*
CAS Registry entry for 414878-87-8 (entered STN May 13, 2002).*
CAS Registry entry for 331978-60-0 (entered STN Apr. 20, 2001).*
CAS Registry entry for 331978-59-7 (entered STN Apr. 20, 2001).*
CAplus record of Thesing et al. Justus Liebigs Annalen der Chemie 1964, 680, 52-59.*
Stahl et al. Handbook of Pharmaceutical Salts, Wiley & Sons, 2008, p. 1-7.*
Serajuddin, Advanced Drug Delivery Reviews 2007, 59, 603-616.*
Berge et al. J. Pharm. Sci. 1977, 66, 1-19.*
CAS Registry entry for Registry No. 1069478-95-0, which entered STN on Nov. 2, 2008.*
CAS Registry entry for Registry No. 414886-30-9, which entered STN on May 13, 2002.*
Registry hits from STN Search.
Registry hits from Scifinder Search.

* cited by examiner

*Primary Examiner* — Joseph Kosack
*Assistant Examiner* — Matthew Coughlin
(74) *Attorney, Agent, or Firm* — Dennis A. Bennett; Cynthia Hathaway

(57) ABSTRACT

The present invention relates to carbazole compounds, pharmaceutical compositions comprising them, and methods which may be useful as inhibitors of $H_1R$ and/or $H_4R$ for the treatment or prevention of inflammatory, autoimmune, allergic, and ocular diseases.

10 Claims, No Drawings

CARBAZOLE INHIBITORS OF HISTAMINE RECEPTORS FOR THE TREATMENT OF DISEASE

This application claims the benefit of priority of U.S. Provision Application No. 61/060,622, filed Jun. 11, 2008.

Disclosed herein are new carbazole compounds and compositions and their application as pharmaceuticals for the treatment of disease. Methods of inhibition of histamine receptor activity in a human or animal subject are also provided for the treatment diseases such as inflammation, asthma, rhinitis, and allergic conjunctivitis.

Histamine, a low molecular weight biogenic amine, is a potent chemical mediator of normal and pathological physiology. Histamine functions as a secreted signal in immune and inflammatory responses, as well as a neurotransmitter. The functions of histamine are mediated through 4 distinct cell surface receptors ($H_1R$, $H_2R$, $H_3R$ and $H_4R$). Histamine receptors vary in expression, signaling, function and histamine affinity, and therefore have different potential therapeutic applications (Zhang M, Thurmond R L, and Dunford P J *Pharmacology & Therapeutics*. 2007).

All 4 histamine receptors are G protein-coupled receptors (GPCRs). Upon histamine or other agonist binding, they activate distinct signaling pathways through different heterotrimeric G proteins. The $H_1R$ couples to the $G_q$ family of G proteins, whose primary signaling cascade induces second messenger calcium mobilization from intracellular stores, followed by multiple downstream effects. $H_1R$ can also increase cyclic GMP (cGMP) production and activate NFκB, a potent, positive transcriptional regulator of inflammation. The $H_2R$ couples to the $G_s$ family of G proteins and increases cyclic AMP (cAMP) formation by stimulating adenylate cyclase, although it can also induce calcium mobilization in some cell types. The $H_3R$ mediates its function through $G_{i/o}$ proteins and decreases cAMP formation by inhibiting adenylate cyclase. Like other $G_{i/o}$-coupled receptors, $H_3R$ also activates the mitogen-activated protein/extracellular-signal regulated protein (MAP/ERK) kinase pathway. $H_4R$ has also been demonstrated to couple to $G_{i/o}$ proteins, with canonical inhibition of cAMP formation and MAP kinase activation. However, H4R also couples to calcium mobilization in certain cell types. In fact, $H_4R$ signaling in mast cells is primarily through calcium mobilization with little to no impact on cAMP formation.

The $H_1R$ is expressed in many cell types, including endothelial cells, most smooth muscle cells, cardiac muscle, central nervous system (CNS) neurons, and lymphocytes. $H_1R$ signaling causes smooth muscle contraction (including bronchoconstriction), vasodilation, and increased vascular permeability, hallmarks of allergic and other immediate hypersensitivity reactions. In the CNS, $H_1R$ activation is associated with wakefulness. Its activation is also associated with pruritus and nociception in skin and mucosal tissues. For many years, the anti-allergic and anti-inflammatory activities of $H_1R$ antagonists have been utilized to treat acute and chronic allergic disorders and other histamine-mediated pathologies, such as itch and hives.

The $H_2R$ is expressed similarly to the $H_1R$, and can also be found in gastric parietal cells and neutrophils. $H_2R$ is best known for its central role in gastric acid secretion but has also been reported to be involved in increased vascular permeability and airway mucus production. Antagonists of H2R are widely used in treating peptic ulcers and gastroesophageal reflux disease. These drugs are also used extensively to reduce the risk of gastrointestinal (GI) bleeding associated with severe upper GI ulcers and GI stress in the inpatient setting.

The $H_3R$ is primarily found in the CNS and peripheral nerves innervating cardiac, bronchial, and GI tissue. $H_3R$ signaling regulates the release of multiple neurotransmitters, such as acetylcholine, dopamine, serotonin, and histamine itself (where it acts as a CNS autoreceptor). In the CNS, $H_3R$ participates in the processes of cognition, memory, sleep, and feeding behaviors. $H_3R$ antagonists may be used potentially for treating cognition disorders (such as Alzheimer's disease), sleep and wakefulness disorders, attention disorders, and metabolic disorders (especially related to obesity).

Existence of the $H_4R$ was predicted in the early 1990s, but its cloning by multiple groups was not reported until 2000. In contrast to the other histamine receptors, the $H_4R$ has a distinctly selective expression profile in bone marrow and on certain types of hematopoietic cells. $H_4R$ signaling modulates the function of mast cells, eosinophils, dendritic cells, and subsets of T cells. The $H_4R$ appears to control multiple behaviors of these cells, such as activation, migration, and cytokine and chemokine production (Zhang M, Thurmond R L, and Dunford P J *Pharmacology & Therapeutics*. 2007).

Of the 4 known histamine receptors, $H_1R$, $H_2R$ and $H_4R$ have been shown clearly to affect inflammation and other immune responses and are or proposed therapeutic targets for treating immune and inflammatory disorders (Jutel M et al., "Immune regulation by histamine," *Curr Opin Immunol.*, 2002 December; 14(6):735-40; Akdis C A and Simons F E, "Histamine receptors are hot in immunopharmacology," *Eur J Pharmacol.*, 2006 Mar. 8; 533(1-3):69-76). The $H_1R$ was the first described histamine receptor, and ligands targeting this receptor were initially developed in the 1930s and in widespread use by the 1940s. Common $H_1R$ antagonist drugs currently approved for use include systemic agents such as diphenhydramine (Benadryl, also used topically), cetirizine (Zyrtec), fexofenadine (Allegra), loratadine (Claritin) and desloratadine (Clarinex), and topical agents such as olopatadine (Patanol, Pataday, Patanase), ketotifen, azelastine (Optivar, Astelin) and epinastine (Elestat). Traditional uses have included allergic diseases and reactions such as asthma, rhinitis, and other chronic obstructive pulmonary disorders, ocular disorders such as allergic conjunctivitis, and pruritus of varying etiologies.

However, $H_1$ receptor antagonists have certain deficiencies as therapeutic agents in the treatment of diseases where histamine is an important mediator. First, their effects are often only moderate and reduce allergic symptoms by only 40 to 50%. In particular, $H_1$ receptor antagonists, especially systemic agents, have little to no effect in relieving nasal congestion. In allergic asthma, despite the fact that histamine levels rapidly increase in the airways and in plasma (correlating with disease severity), $H_1$ receptor antagonists have largely failed as a therapeutic strategy, though some effect is seen with administration during the priming phase as opposed to the challenge phase (Thurmond R L et al., *Nat Rev Drug Discov,* 2008, 7:41-53). Additionally, although the efficacy of $H_1$ receptor antagonists against pruritus in acute urticarias, associated with hives and insect stings, and in chronic idiopathic urticaria is well proven, $H_1R$ antagonists are mostly ineffective in the treatment of atopic dermatitis-associated pruritus, with the only modest benefits derived from some first-generation compounds likely a consequence of their sedative properties (Sharpe, G. R. & Shuster, S. *Br. I Dermatol.* 1993, 129:575-9). Finally, sedation caused by $H_1R$ antagonists that cross the blood-brain barrier, among other side effects, limits the utility of many $H_1R$ antagonists in diseases for which they would otherwise be efficacious. These deficiencies render H₁R antagonists amenable to replacement by or supplementation with other agents.

Consequently, recent attention has focused on the more recently discovered H₄ receptor as a therapeutic target. Given the ability of H₄R to modulate the cellular function of eosinophils, mast cells, dendritic cells and T cells (Zhang M et al., "The histamine H(4) receptor: a novel modulator of inflammatory and immune disorders," *Pharmacol Ther.*, 2007 March; 113(3):594-606), it is natural to speculate that the H₄R may be involved in various inflammatory diseases, and that H₄R antagonists would have therapeutic potential. Indeed, both in vitro and in vivo evidence has been demonstrated for the utility of H₄R antagonists as anti-inflammatory agents in inflammatory bowel disease (IBD (Sander L E et al., *Gut* 2006; 55:498-504). The finding that H₄ receptor antagonists inhibit histamine-induced migration of mast cells and eosinophils in vitro and in vivo, both of which are important effector cells in the allergic response, raises the possibility that this class of compounds could reduce the allergic hyper-responsiveness developed upon repeated exposure to antigens, which is characterized by an increase in the number of mast cells and other inflammatory cells in the nasal and bronchial mucosa (Fung-Leung W P et al., *Curr Opin Inves Drugs*, 2004 5:11 1174-1182). In contrast to some of the H₁R antagonists, H₄R antagonists given during the allergen challenge phase of a mouse model of asthma are equally effective to those given during sensitization (Thurmond R L et al., *Nat Rev Drug Discov*, 2008, 7:41-53). In two recent mouse studies, a selective H₄R agonist was shown to induce itch, whereas these responses, and those of histamine, were blocked by pretreatment with H₄R antagonists. Similarly, histamine or H4 receptor agonist-induced itch was markedly attenuated in H4 receptor-deficient animals (Dunford, P. J. et al., *J. Allergy Clin. Immunol*, 2007, 119:176-183).

Current research efforts include both a focus on H4R selective agents and an alternate path toward dual H₁R/H₄R agents. Johnson & Johnson have developed a well-characterized H₄R antagonist, JNJ-7777120, which is 1000-fold selective over H₁, H₂, and H₃ receptors, and equipotent across human and several nonhuman species. An exemplary H₁R/H₄R dual agent has yet to publish as of the time of this writing, and the ideal proportion of H₁R versus H₄R antagonism is a nascent topic of debate. Nevertheless, the concept of dual activity via a single agent is well-precedented, and the design of multiply active ligands is a current topic in pharmaceutical discovery (Morphy R and Rankovic Z, *J Med Chem*. 2005; 48(21):6523-43). Additional reports have shown potential for H₄R antagonists, or potentially, H₁R/H₄R dual antagonists, in the treatment of metabolic disorders such as obesity (Jorgensen E et al., *Neuroendocrinology*. 2007; 86(3):210-4), vascular or cardiovascular diseases such as atherosclerosis (Tanihide A et al., *TCM* 2006: 16(8): 280-4), inflammation and pain (Coruzzi G et al., *Eur J Pharmacol*. 2007 Jun. 1; 563(1-3):240-4), rheumatoid arthritis (Grzybowska-Kowalczyk A et al., *Inflamm Res.* 2007 April; 56 Suppl 1:S59-60) and other inflammatory and autoimmune diseases including systemic lupus erythematosus (Zhang M, Thurmond R L, and Dunford P J *Pharmacology & Therapeutics*. 2007). What is clear is that a need still exists in the art for improved and varied antihistamines for the treatment of disease, and that compounds with H₄R and/or H₁R/H₄R antagonist activity may fill this need.

Novel compounds and pharmaceutical compositions, certain of which have been found to inhibit the histamine type-1 receptor (H₁R) and/or the histamine type-4 receptor (H₄R) have been discovered, together with methods of synthesizing and using the compounds including methods for the treatment of histamine receptor-mediated diseases in a patient by administering the compounds.

In certain embodiments of the present invention, compounds have structural Formula I:

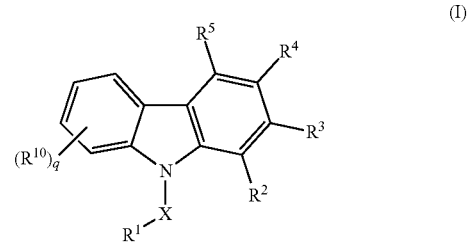

or a salt, ester, or prodrug thereof, wherein:

X is chosen from lower alkylene, lower alkenylene, and lower alkynylene, any of which may be optionally substituted with one or more substituents chosen from halogen, hydroxy, and cyano;

$R^1$ is chosen from hydrogen, hydroxy, lower cycloalkyl, lower heterocycloalkyl, lower amino, lower thio, lower carboxy, lower amido, and lower acyl;

one of $R^2$, $R^3$, $R^4$, and $R^5$ is a substituent having the following structural formula

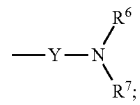

the other three of $R^2$, $R^3$, $R^4$, and $R^5$, and each $R^{10}$, are independently chosen from hydrogen, halogen, hydroxy, alkyl, alkenyl, alkynyl, heteroalkyl, cycloalkyl, aryl, heterocycloalkyl, heteroaryl, aralkyl, heteroaralkyl, alkoxy, haloalkoxy, haloalkyl, amino, amido, acyl, carboxyl, nitro, and cyano, any of which may be optionally substituted;

Y is chosen from $[C(R^8)(R^9)]_m$ and $[C(R^8)(R^9)]_n Z[C(R^8)(R^9)]_p$;

Z is chosen from N, O, S, S(O), and S(O)₂;

m is an integer from 1 to 6;

n and p are each independently an integer from 0 to 3;

q is an integer from 0 to 4;

$R^6$ and $R^7$ are independently chosen from hydrogen, alkyl, alkenyl, alkynyl, heteroalkyl, cycloalkyl, aryl, heterocycloalkyl, heteroaryl, aralkyl, heteroaralkyl, alkoxy, haloalkoxy, acyl, and carboxyl, any of which may be optionally substituted; or alternatively, $R^6$ and $R^7$, together with the nitrogen to which they are attached may combine to form cycloalkyl, aryl, heterocycloalkyl, or heteroaryl, any of which may be optionally substituted; and $R^8$ and $R^9$ are independently chosen from hydrogen, halogen, hydroxy, cyano, lower alkyl, lower haloalkyl, and lower heteroalkyl.

Certain compounds disclosed herein may possess useful histamine receptor inhibitory activity, and may be used in the treatment or prophylaxis of a disease or condition in which H₁R and/or H₄R plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting $H_1R$ and/or $H_4R$. Other embodiments provide methods for treating a $H_1R$- and/or $H_4R$-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the inhibition of $H_1R$ and/or $H_4R$.

In certain embodiments, compounds have Formula I wherein $R^6$ and $R^7$, together with the nitrogen to which they are attached combine to form optionally substituted heterocycloalkyl.

In further embodiments, said optionally substituted heterocycloalkyl is optionally substituted monocyclic heterocycloalkyl.

In certain embodiments,
n and p are both 0; and
$R^8$ and $R^9$ are hydrogen.
In certain embodiments, Y is $[C(R^8)(R^9)]_m$.
In further embodiments,
m is 1; and
$R^8$ and $R^9$ are hydrogen.
In certain embodiments,
one of $R^2$, $R^3$, $R^4$, and $R^5$ is a substituent having the following structural formula

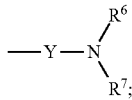

and
the other three of $R^2$, $R^3$, $R^4$, and $R^5$, and each $R^{10}$, are independently chosen from hydrogen, halogen, hydroxy, lower alkyl, lower alkenyl, lower alkynyl, lower alkoxy, lower haloalkyl, lower haloalkoxy, lower amino, lower amido, lower acyl, lower carboxyl, nitro, and cyano.

In further embodiments, the other three of $R^2$, $R^3$, $R^4$, and $R^5$, and each $R^{10}$, are independently chosen from hydrogen, halogen, hydroxy, lower alkyl, lower alkoxy, lower haloalkyl, lower haloalkoxy, and cyano.

In yet further embodiments, the other three of $R^2$, $R^3$, $R^4$, and $R^5$ are independently chosen from hydrogen, halogen, hydroxy, methyl, ethyl, methoxy, fluoromethyl, perfluoromethyl, fluoromethoxy, perfluoromethoxy, and cyano.

In yet further embodiments, q is 0.

In yet further embodiments, the other three of $R^2$, $R^3$, $R^4$, and $R^5$ are hydrogen.

In certain embodiments, X is lower alkylene.

In further embodiments, X is ethylene.

In yet further embodiments, said ethylene is unsubstituted, and $R^1$ is chosen from hydrogen, hydroxy, lower cycloalkyl, lower heterocycloalkyl, lower amino, lower thio, lower carboxy, lower amido, and lower acyl.

In yet further embodiments, $R^1$ is hydrogen.

In certain embodiments, the disease to be treated is chosen from an inflammatory disease, an autoimmune disease, an allergic disorder, an otic disorder, and an ocular disorder.

In further embodiments, said disease is chosen from asthma, rhinitis, eustacian tube itching, and allergic conjunctivitis.

In certain embodiments, administration of compounds is topical and is to the eye.

Also provided herein is a method of treatment of a $H_1R$ and/or $H_4R$-mediated disease comprising the administration, to a patient in need of such treatment, of a therapeutically effective amount of a compound as disclosed herein. Further provided herein is a method of treatment of a $H_1R$ and/or $H_4R$-mediated disease comprising the administration, to a patient in need of such treatment, of a therapeutically effective amount of a compound of Formula I. Yet further provided herein is a method of treatment of a $H_1R$ and/or $H_4R$-mediated disease comprising the administration, to a patient in need of such treatment, of a therapeutically effective amount of a compound chosen from Examples 1-34.

Also provided herein is a method of treatment of a $H_1R$ and/or $H_4R$-mediated disease comprising the administration, to a patient in need of such treatment, of
i. a therapeutically effective amount of a compound as disclosed herein; and
ii. another therapeutic agent.

Further provided herein is a method of treatment of a $H_1R$ and/or $H_4R$-mediated disease comprising the administration, to a patient in need of such treatment, of
i. a therapeutically effective amount of a compound of Formula I; and
ii. another therapeutic agent.

Yet further provided herein is a method of treatment of a $H_1R$ and/or $H_4R$-mediated disease comprising the administration, to a patient in need of such treatment, of
i. a therapeutically effective amount of a compound chosen from Examples 1-34; and
ii. another therapeutic agent.

In certain embodiments, the disease is mediated by $H_4R$.

In certain embodiments, the disease is mediated by both $H_1R$ and $H_4R$.

Also provided herein is a method of inhibition of $H_1R$ and/or $H_4R$ comprising contacting $H_1R$ and/or $H_4R$ with a compound as disclosed herein. Further provided herein is a method of inhibition of $H_1R$ and/or $H_4R$ comprising contacting $H_1R$ and/or $H_4R$ with a compound of Formula I. Yet further provided herein is a method of inhibition of $H_1R$ and/or $H_4R$ comprising contacting $H_1R$ and/or $H_4R$ with a compound chosen from Examples 1-34.

In certain embodiments, the inhibition is of $H_4R$.

In certain embodiments, the inhibition is of both $H_1R$ and $H_4R$.

In certain embodiments, the compound has structural Formula II:

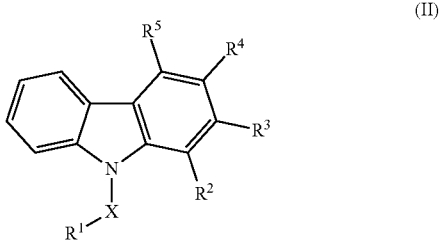

or a salt, ester, or prodrug thereof, wherein
X is chosen from lower alkylene, lower alkenylene, and lower alkynylene, any of which may be optionally substituted with one or more substituents chosen from halogen, hydroxy, and cyano;
$R^1$ is chosen from hydrogen, hydroxy, lower cycloalkyl, lower heterocycloalkyl, lower amino, thio, carboxy, amido, and acyl;

three of $R^2$, $R^3$, $R^4$, and $R^5$ are hydrogen, and one of $R^2$, $R^3$, $R^4$, and $R^5$ is a substituent having the following structural formula

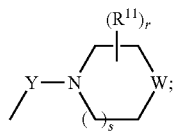

Y is chosen from lower alkylene, N, O, S, S(O), and $S(O)_2$;
W is chosen from C, N, and O;
r is 0-3;
s is 0 or 1;
each $R^{11}$ is individually chosen from hydrogen, hydroxy, lower hydroxyalkyl, lower alkyl, halogen, lower haloalkyl, lower alkoxy, lower haloalkoxy, monocyclic 5-membered heteroaryl, $C(O)OR^{12}$, $C(O)N(R^{12})(R^{13})$, lower alkoxy, perfluoromethyl, and perfluoromethoxy; and
$R^{12}$ and $R^{13}$ are individually chosen from hydrogen, lower alkyl, lower cycloalkyl, lower cycloalkylalkyl, lower heterocycloalkyl, lower heterocycloalkylalkyl, lower heteroaryl, lower heteroarylalkyl, any of which may be optionally substituted with one or more substituents chosen from halogen, hydroxy, cyano, lower alkyl, lower alkenyl, lower alkynyl, lower heteroalkyl, lower alkoxy, lower haloalkyl, and lower haloalkoxy.

In certain embodiments, X is lower alkylene.
In further embodiments, $R^1$ is chosen from hydrogen and lower amino.
In yet further embodiments, X is ethylene and $R^1$ is hydrogen.
In yet further embodiments, Y is lower alkylene.
In yet further embodiments, Y is methylene.
In yet further embodiments, r is 0, 1, or 2.
In yet further embodiments, $R^{12}$ and $R^{13}$ are individually chosen from hydrogen and lower alkyl.
In yet further embodiments, $R^{11}$ is chosen from hydrogen, lower alkyl, and monocyclic 5-membered heteroaryl.
In yet further embodiments, $R^{11}$ is monocyclic 5-membered heteroaryl.
In yet further embodiments, said monocyclic 5-membered heteroaryl contains nitrogen and carbon atoms only.
In yet further embodiments, $R^2$, $R^3$, and $R^5$ are hydrogen.
In yet further embodiments, compounds have structural Formula IIIa:

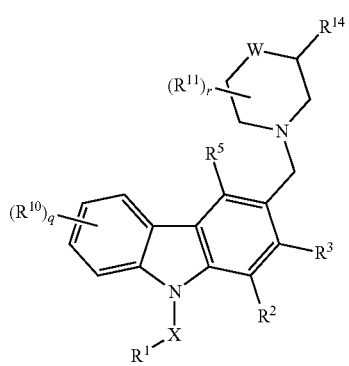

(IIIa)

or a salt, ester, or prodrug thereof, wherein
X is chosen from lower alkyl, lower alkenyl, and lower alkynyl, any of which may be optionally substituted with one or more substituents chosen from halogen, hydroxy, and cyano;
$R^1$ is chosen from hydrogen, hydroxy, lower cycloalkyl, lower heterocycloalkyl, lower amino, thio, carboxy, amido, and acyl;
W is chosen from C, N, and O;
q is an integer from 0 to 4;
$R^2$, $R^3$, and $R^5$, and each $R^{10}$, are independently chosen from hydrogen, halogen, hydroxy, alkyl, alkenyl, alkynyl, heteroalkyl, cycloalkyl, aryl, heterocycloalkyl, heteroaryl, aralkyl, heteroaralkyl, alkoxy, haloalkoxy, haloalkyl, amino, amido, acyl, carboxyl, nitro, and cyano, any of which may be optionally substituted;
r is 0-3;
each $R^{11}$ is individually chosen from hydrogen, halogen, hydroxy, lower hydroxyalkyl, lower alkyl, halogen, lower haloalkyl, lower alkoxy, lower haloalkoxy, monocyclic 5-membered heteroaryl, $C(O)OR^{12}$, $C(O)N(R^{12})(R^{13})$, perfluoromethyl, and perfluoromethoxy;
$R^{12}$ and $R^{13}$ are individually chosen from hydrogen, lower alkyl, lower cycloalkyl, lower cycloalkylalkyl, lower heterocycloalkyl, lower heterocycloalkylalkyl, lower heteroaryl, lower heteroarylalkyl, any of which may be optionally substituted with one or more substituents chosen from halogen, hydroxy, cyano, lower alkyl, lower alkenyl, lower alkynyl, lower heteroalkyl, lower alkoxy, lower haloalkyl, and lower haloalkoxy; and
$R^{14}$ is a five-membered monocyclic heteroaryl.

In yet further embodiments, compounds have structural Formula III:

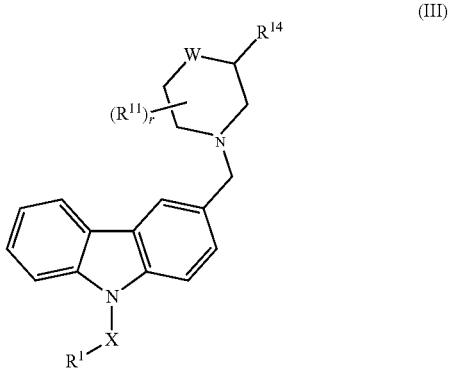

(III)

or a salt, ester, or prodrug thereof, wherein
X is chosen from lower alkyl, lower alkenyl, and lower alkynyl, any of which may be optionally substituted with one or more substituents chosen from halogen, hydroxy, and cyano;
$R^1$ is chosen from hydrogen, hydroxy, lower cycloalkyl, lower heterocycloalkyl, lower amino, thio, carboxy, amido, and acyl;
W is chosen from C, N, and O;
r is 0-3;
each $R^{11}$ is individually chosen from hydrogen, halogen, hydroxy, lower hydroxyalkyl, lower alkyl, halogen, lower haloalkyl, lower alkoxy, lower haloalkoxy, monocyclic 5-membered heteroaryl, $C(O)OR^{12}$, $C(O)N(R^{12})(R^{13})$, perfluoromethyl, and perfluoromethoxy;
$R^{12}$ and $R^{13}$ are individually chosen from hydrogen, lower alkyl, lower cycloalkyl, lower cycloalkylalkyl, lower heterocycloalkyl, lower heterocycloalkylalkyl, lower heteroaryl, lower heteroarylalkyl, any of which may be optionally substituted with one or more substituents chosen from halogen, hydroxy, cyano, lower alkyl, lower alkenyl, lower alkynyl, lower heteroalkyl, lower alkoxy, lower haloalkyl, and lower haloalkoxy; and $R^{14}$ is a five-membered monocyclic heteroaryl.

The compound as recited in claim 14 wherein:
X is lower alkyl;
$R^1$ is hydrogen;
W is chosen from N, C, O;
each $R^{11}$ is individually chosen from hydroxyalkyl, lower alkyl, monocyclic 5-membered heteroaryl, $C(O)OR^{12}$, and $C(O)N(R^{12})(R^{13})$; and
$R^{12}$ and $R^{13}$ are chosen from hydrogen and lower alkyl.

In further embodiments, compounds have structural formula IV:

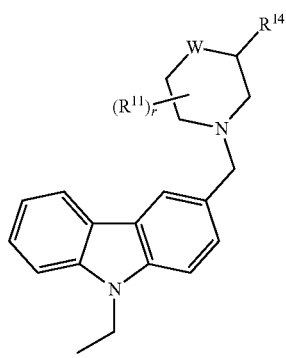

IV or a salt, ester, or prodrug thereof, wherein
W is chosen from C, N, and O;
r is 0-3;
each $R^{11}$ is individually chosen from hydrogen, halogen, hydroxy, lower hydroxyalkyl, lower alkyl, halogen, lower haloalkyl, lower alkoxy, lower haloalkoxy, monocyclic 5-membered heteroaryl, $C(O)OR^{12}$, $C(O)N(R^{12})(R^{13})$, perfluoromethyl, and perfluoromethoxy;
$R^{12}$ and $R^{13}$ are individually chosen from hydrogen, lower alkyl, lower cycloalkyl, lower cycloalkylalkyl, lower heterocycloalkyl, lower heterocycloalkylalkyl, lower heteroaryl, lower heteroarylalkyl, any of which may be optionally substituted with one or more substituents chosen from halogen, hydroxy, cyano, lower alkyl, lower alkenyl, lower alkynyl, lower heteroalkyl, lower alkoxy, lower haloalkyl, and lower haloalkoxy; and
$R^{14}$ is a five-membered monocyclic heteroaryl.

In further embodiments, $R^{12}$ and $R^{13}$ are individually chosen from hydrogen and lower alkyl.

In yet further embodiments, $R^{11}$ is chosen from hydrogen, lower alkyl, and monocyclic 5-membered heteroaryl.

In yet further embodiments, $R^{11}$ is monocyclic 5-membered heteroaryl.

In yet further embodiments, said monocyclic 5-membered heteroaryl contains nitrogen and carbon atoms only.

In yet further embodiments, r is 0 or 1.

In other embodiments is provided a compound chosen from Examples 1-34.

In further embodiments, the compound is chosen from Examples 1, 10-24, and 26-33.

In other embodiments is provided a compound as disclosed herein for use as a medicament. In further embodiments is provided a compound of any of Formulas I-IV above for use as a medicament. In further embodiments is provided a compound chosen from Examples 1-34 for use as a medicament.

In other embodiments is provided a compound as disclosed herein for use in the manufacture of a medicament for the prevention or treatment of a disease or condition ameliorated by the inhibition of $H_1R$ and/or $H_4R$. In further embodiments is provided a compound of any of Formulas I-IV above for use in the manufacture of a medicament for the prevention or treatment of a disease or condition ameliorated by the inhibition of $H_1R$ and/or $H_4R$. In further embodiments is provided a compound chosen from Examples 1-34 for the prevention or treatment of a disease or condition ameliorated by the inhibition of $H_1R$ and/or $H_4R$.

As used herein, the terms below have the meanings indicated.

When ranges of values are disclosed, and the notation "from $n_1$ ... to $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety where the atom attached to the carbonyl is carbon. An "acetyl" group refers to a —$C(O)CH_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon group having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—), (—C::C—)]. Examples of suitable alkenyl groups include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether group, wherein the term alkyl is as defined below. Examples of suitable alkyl ether groups include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl group containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) group wherein the term alkyl is as defined above and wherein the sulfur may be singly or doubly oxidized. Examples of suitable alkyl thioether groups include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon group having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl groups include ethynyl, propynyl, hydroxypropanyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)NRR' group with R and R' as defined herein. The term "N-amido" as used herein, alone or in combination, refers to a RC(O)NR'— group, with R and R' as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl group derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent group $C_6H_4$= derived from benzene. Examples include benzothiophene and benzimidazole.

The term "carbamate," as used herein, alone or in combination, refers to an ester of carbamic acid (—NRCOO—) which may be attached to the parent molecular moiety from either the nitrogen or acid end, wherein R is as defined herein, and which may be optionally substituted as defined herein.

The term "O-carbamyl" as used herein, alone or in combination, refers to a —OC(O)NRR', group with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl group having the meaning as defined above wherein one or more hydrogens are replaced with a halogen. Specifically embraced are monohaloalkyl, dihaloalkyl and polyhaloalkyl groups. A monohaloalkyl group, for one example, may have an iodo, bromo, chloro or fluoro atom within the group. Dihalo and polyhaloalkyl groups may have two or more of the same halo atoms or a combination of different halo groups. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon group, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur. In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, which may be optionally substituted as provided.

The term "lower heteroalkyl," as used herein, alone or in combination, refers to a stable straight or branched chain, or cyclic hydrocarbon group, or combinations thereof, fully saturated or containing from 1 to 3 degrees of unsaturation, consisting of one to six atoms in which one to three may be heteroatoms selected from the group consisting of O, N, and S, and the remaining atoms are carbon. The nitrogen and sulfur atoms may optionally be oxidized and the nitrogen heteroatom may optionally be quaternized. The heteroatom(s) O, N and S may be placed at any interior or terminal position of the heteroalkyl group. Up to two heteroatoms may be consecutive, such as, for example, —CH$_2$—NH—OCH$_3$.

The term "lower heteroaryl," as used herein, alone or in combination, means either 1) monocyclic heteroaryl comprising five or six ring members, of which between one and four said members may be heteroatoms selected from the group consisting of O, S, and N, or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently selected from the group consisting of hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer to the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(O)$_2$NR'— group with R and R' as defined herein.

The term "S-sulfonamido" refers to a —S(O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O) CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, ... n), every substituent, and every term should be understood to be independent of every other in terms of selection from a group. Should any variable, substituent, or term (e.g., aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "inhibition" (and by extension, "inhibitor") as used herein encompasses all forms of functional protein (enzyme, kinase, receptor, channel, etc., for example) inhibition, including neutral antagonism, inverse agonism, competitive inhibition, and non-competitive inhibition (such as allosteric inhibition). Inhibition may be phrased in terms of an $IC_{50}$, defined below.

In certain embodiments, "$H_1R$ inhibitor" is used herein to refer to a compound that exhibits an $IC_{50}$ with respect to the histamine type-1 receptor of no more than about 100 μM and more typically not more than about 50 μM, as measured in the in vitro histamine receptor cell-based assays described generally hereinbelow. In certain embodiments, inhibitors will have an $IC_{50}$ of 10 μM or below. In further embodiments, inhibitors will have an $IC_{50}$ of 1 μM or below. Similarly, "$H_4R$ inhibitor" is used herein to refer to a compound that exhibits an $IC_{50}$ with respect to the histamine type-4 receptor of no more than about 100 μM and more typically not more than about 50 μM, as measured in the in vitro histamine receptor cell-based assays described generally hereinbelow. In certain embodiments, inhibitors will have an $IC_{50}$ of 10 μM or below. In further embodiments, inhibitors will have an $IC_{50}$ of 1 μM or below. A "$H_1/H_4$ inhibitor" is used herein to refer to a compound that exhibits an $IC_{50}$ with respect to both the histamine type-1 receptor and the histamine type-4 receptor of no more than about 100 μM and more typically not more than about 50 μM, as measured in the in vitro histamine receptor cell-based assays described generally hereinbelow; the amount of inhibition need not be equivalent at each receptor, but should not be negligible. In certain embodiments, inhibitors will have an $IC_{50}$ of 10 μM or below. In further embodiments, inhibitors will have an $IC_{50}$ of 1 μM or below. In certain embodiments, such as, for example, in the case of an in vitro ligand-binding assay protocol, "$IC_{50}$" is that concentration of inhibitor which is required to displace a natural ligand or reference standard to a half-maximal level. In other embodiments, such as, for example, in the case of certain cellular or in vivo protocols which have a functional readout, "$IC_{50}$" is that concentration of inhibitor which reduces the activity of a functional protein (e.g., $H_1R$ and/or $H_4R$) to a half-maximal level. Certain compounds disclosed herein have been discovered to exhibit inhibitory activity against $H_1R$ and/or $H_4R$. In certain embodiments, compounds will exhibit an $IC_{50}$ with respect to $H_1R$ and/or $H_4R$ of no more than about 10 μM; in further embodiments, compounds will exhibit an $IC_{50}$ with respect to $H_1R$ and/or $H_4R$ of no more than about 5 μM; in yet further embodiments, compounds will exhibit an $IC_{50}$ with respect to $H_1R$ and/or $H_4R$ of not more than about 1 μM; in yet further embodiments, compounds will exhibit an $IC_{50}$ with respect to $H_1R$ and/or $H_4R$ of not more than about 200 nM, as measured in the $H_1R$ and/or $H_4R$ assay described herein.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Topical ophthalmic, otic, and nasal formulations of the present invention may comprise excipients in addition to the active ingredient. Excipients commonly used in such formulations include, but are not limited to, tonicity agents, preservatives, chelating agents, buffering agents, and surfactants. Other excipients comprise solubilizing agents, stabilizing agents, comfort-enhancing agents, polymers, emollients, pH-adjusting agents and/or lubricants. Any of a variety of excipients may be used in formulations of the present invention including water, mixtures of water and water-miscible solvents, such as C1-C7-alkanols, vegetable oils or mineral oils comprising from 0.5 to 5% non-toxic water-soluble polymers, natural products, such as alginates, pectins, tragacanth, karaya gum, guar gum, xanthan gum, carrageenin, agar and acacia, starch derivatives, such as starch acetate and hydroxypropyl starch, and also other synthetic products such as polyvinyl alcohol, polyvinylpyrrolidone, polyvinyl methyl ether, polyethylene oxide, preferably cross-linked polyacrylic acid and mixtures of those products. The concentration of the excipient is, typically, from 1 to 100,000 times the concentration of the active ingredient. In preferred embodiments, the excipients to be included in the formulations are typically selected on the basis of their inertness towards the active ingredient component of the formulations.

Relative to ophthalmic, otic, and nasal formulations, suitable tonicity-adjusting agents include, but are not limited to, mannitol, sodium chloride, glycerin, sorbitol and the like. Suitable buffering agents include, but are not limited to, phosphates, borates, acetates and the like. Suitable surfactants include, but are not limited to, ionic and nonionic surfactants (though nonionic surfactants are preferred), RLM 100, POE 20 cetylstearyl ethers such as Procol® CS20 and poloxamers such as Pluronic® F68.

The formulations set forth herein may comprise one or more preservatives. Examples of such preservatives include p-hydroxybenzoic acid ester, sodium perborate, sodium chlorite, alcohols such as chlorobutanol, benzyl alcohol or phenyl ethanol, guanidine derivatives such as polyhexamethylene biguanide, sodium perborate, polyquaternium-1, amino alcohols such as AMP-95, or sorbic acid. In certain embodiments, the formulation may be self-preserved so that no preservation agent is required.

For ophthalmic, otic, or nasal administration, the formulation may be a solution, a suspension, or a gel. In preferred aspects, the formulations are for topical application to the eye, nose, or ear in aqueous solution in the form of drops. The term "aqueous" typically denotes an aqueous formulation wherein the formulation is >50%, more preferably >75% and in particular >90% by weight water. These drops may be delivered from a single dose ampoule which may preferably be sterile and thus render bacteriostatic components of the formulation unnecessary. Alternatively, the drops may be delivered from a multi-dose bottle which may preferably comprise a device which extracts any preservative from the formulation as it is delivered, such devices being known in the art.

For ophthalmic disorders, components of the invention may be delivered to the eye as a concentrated gel or a similar vehicle, or as dissolvable inserts that are placed beneath the eyelids.

The formulations of the present invention that are adapted for topical administration to the eye are preferably isotonic, or slightly hypotonic in order to combat any hypertonicity of tears caused by evaporation and/or disease. This may require a tonicity agent to bring the osmolality of the formulation to a level at or near 210-320 milliosmoles per kilogram (mOsm/kg). The formulations of the present invention generally have an osmolality in the range of 220-320 mOsm/kg, and preferably have an osmolality in the range of 235-300 mOsm/kg. The ophthalmic formulations will generally be formulated as sterile aqueous solutions.

In certain ophthalmic embodiments, the compositions of the present invention are formulated with one or more tear substitutes. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; vinyl polymers, such as polyvinyl alcohol; and carbomers, such as carbomer 934P, carbomer 941, carbomer 940 and carbomer 974P. Certain formulations of the present invention may be used with contact lenses or other ophthalmic products.

In certain embodiments, formulations are prepared using a buffering system that maintains the formulation at a pH of about 4.5 to a pH of about 8. A most preferred formulation pH is from 7 to 8.

In certain embodiments, a formulation of the present invention is administered once a day. However, the formulations may also be formulated for administration at any frequency of administration, including once a week, once every 5 days, once every 3 days, once every 2 days, twice a day, three times a day, four times a day, five times a day, six times a day, eight times a day, every hour, or any greater frequency. Such dosing frequency is also maintained for a varying duration of time depending on the therapeutic regimen. The duration of a particular therapeutic regimen may vary from one-time dosing to a regimen that extends for months or years. The formulations are administered at varying dosages, but typical dosages are one to two drops at each administration, or a comparable amount of a gel or other formulation. One of ordinary skill in the art would be familiar with determining a therapeutic regimen for a specific indication.

Gels for topical or transdermal administration may comprise, generally, a mixture of volatile solvents, nonvolatile solvents, and water. In certain embodiments, the volatile solvent component of the buffered solvent system may include lower (C1-C6) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, galactomannan polymers (such as guar and derivatives thereof) and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as stearic or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating $H_1R$ and/or $H_4R$-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of $H_1R$ and/or $H_4R$-mediated disorders.

Specific diseases to be treated by the compounds, compositions, and methods disclosed herein include inflammation and related diseases, including autoimmune diseases. The compounds are useful to treat arthritis, including but not limited to rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis. The compounds are also useful in treating osteoporosis and other related bone disorders. These compounds can also be used to treat gastrointestinal conditions such as reflux esophagitis, diarrhea, inflammatory bowel disease, Crohn's disease, gastritis, irritable bowel syndrome and ulcerative colitis. The compounds may also be used in the treatment of upper respiratory inflammation, such as, but not limited to, allergic rhinitis, seasonal rhinitis, perennial rhinitis, and nasal polyps, as well as pulmonary inflammation, such as that associated with viral infections and cystic fibrosis. In addition, compounds disclosed herein are also useful in organ transplant patients either alone or in combination with conventional immunomodulators.

Moreover, compounds disclosed herein may be used in the treatment of tendonitis, bursitis, skin-related conditions such as psoriasis, eczema, burns, sunburn, dermatitis, acute urticarias, chronic idiopathic urticaria, vitaligo, pancreatitis, hepatitis, and acute or chronic pruritus associated with skin-localized or systemic diseases and disorders.

Further, the compounds disclosed herein can be used to treat respiratory diseases, including therapeutic methods of use in medicine for preventing and treating a respiratory disease or condition including: asthmatic conditions including allergen-induced asthma, exercise-induced asthma, pollution-induced asthma, cold-induced asthma, and viral-induced-asthma; chronic obstructive pulmonary diseases including chronic bronchitis with normal airflow, chronic bronchitis with airway obstruction (chronic obstructive bronchitis), emphysema, asthmatic bronchitis, and bullous disease; and other pulmonary diseases involving inflammation including bronchioectasis cystic fibrosis, pigeon fancier's disease, farmer's lung, acute respiratory distress syndrome, pneumonia, aspiration or inhalation injury, fat embolism in the lung, acidosis inflammation of the lung, acute pulmonary edema, acute mountain sickness, acute pulmonary hypertension, persistent pulmonary hypertension of the newborn, perinatal aspiration syndrome, hyaline membrane disease, acute pulmonary thromboembolism, heparin-protamine reactions, sepsis, status asthamticus and hypoxia.

The compounds disclosed herein are also useful in treating tissue damage in such diseases as vascular diseases, periarteritis nodosa, thyroiditis, sclerodoma, rheumatic fever, type I diabetes, neuromuscular junction disease including myasthenia gravis, white matter disease including multiple sclerosis, sarcoidosis, nephritis, nephrotic syndrome, Behcet's syndrome, polymyositis, gingivitis, periodontis, hypersensitivity, and swelling occurring after injury.

The compounds disclosed herein can be used in the treatment of otic diseases and otic allergic disorders, including eustachian tube itching.

The compounds disclosed herein can be used in the treatment of ophthalmic diseases, such as ophthalmic allergic disorders, including allergic conjunctivitis, vernal conjunctivitis, vernal keratoconjunctivitis, and giant papillary conjunctivitis, dry eye, glaucoma, glaucomatous retinopathy, diabetic retinopathy, retinal ganglion degeneration, ocular ischemia, retinitis, retinopathies, uveitis, ocular photophobia, and of inflammation and pain associated with acute injury to the eye tissue. The compounds can also be used to treat post-operative inflammation or pain as from ophthalmic surgery such as cataract surgery and refractive surgery. In certain embodiments, the compounds of the present invention are used to treat an allergic eye disease selected from the group consisting of allergic conjunctivitis; vernal conjunctivitis; vernal keratoconjunctivitis; and giant papillary conjunctivitis.

Compounds disclosed herein are useful in treating patients with inflammatory pain such as reflex sympathetic dystrophy/causalgia (nerve injury), peripheral neuropathy (including diabetic neuropathy), and entrapment neuropathy (carpel tunnel syndrome). The compounds are also useful in the treatment of pain associated with acute herpes zoster (shingles), postherpetic neuralgia (PHN), and associated pain syndromes such as ocular pain. Pain indications include, but are not limited to, pain resulting from dermal injuries and pain-related disorders such as tactile allodynia and hyperalgesia. The pain may be somatogenic (either nociceptive or neuropathic), acute and/or chronic.

The present compounds may also be used in co-therapies, partially or completely, in place of other conventional anti-inflammatory therapies, such as together with steroids, NSAIDs, COX-2 selective inhibitors, 5-lipoxygenase inhibitors, $LTB_4$ antagonists and $LTA_4$ hydrolase inhibitors. The compounds disclosed herein may also be used to prevent tissue damage when therapeutically combined with antibacterial or antiviral agents.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

All references, patents or applications, U.S. or foreign, cited in the application are hereby incorporated by reference as if written herein in their entireties. Where any inconsistencies arise, material literally disclosed herein controls.

General Synthetic Methods for Preparing Compounds

The following schemes can be used to practice the present invention.

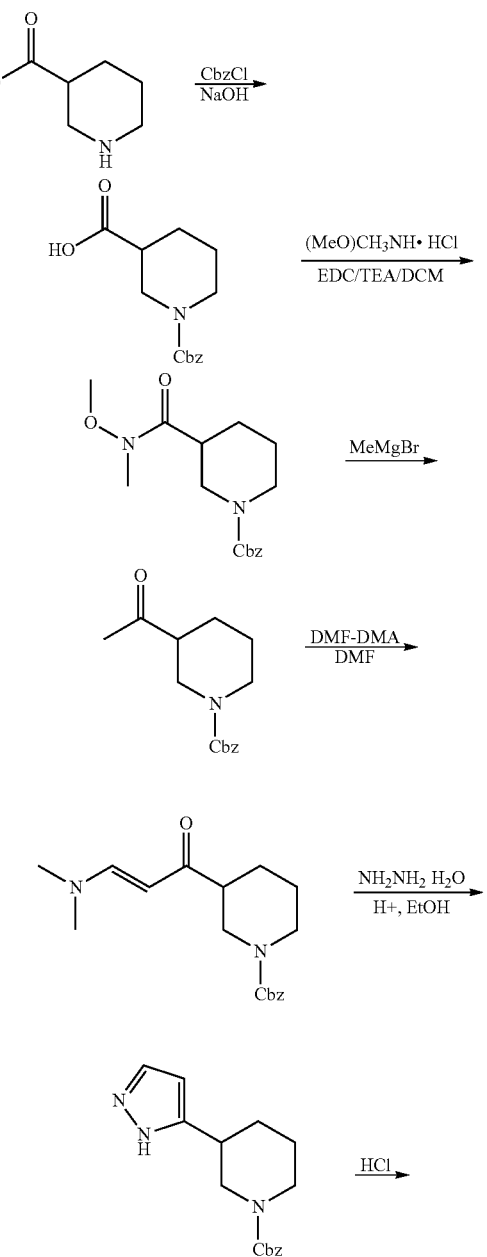

-continued

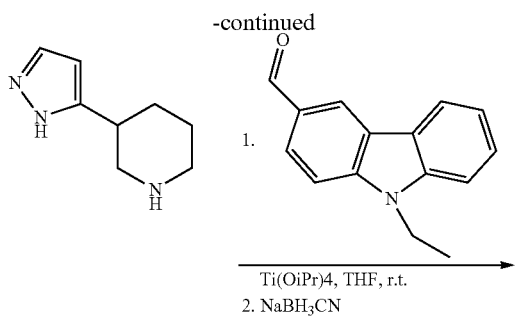

The invention is further illustrated by the following examples, which may be made by the methods below or by methods known in the art. Additionally, these compounds may be commercially available.

EXAMPLE 1

3-((3-(1H-pyrazol-5-yl)piperidin-1-yl)methyl)-9-ethyl-9H-carbazole

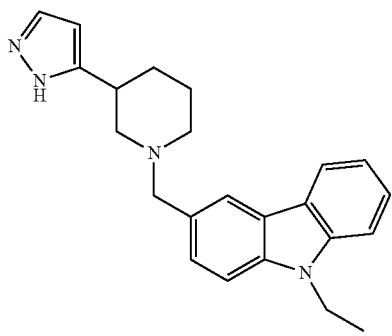

Step 1.
1-(Benzyloxycarbonyl)piperidine-3-carboxylic

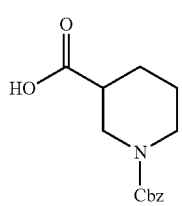

A 500-mL 4-necked round-bottom flask was charged with a solution of NaOH (8 g, 198.00 mmol, 1.00 equiv, 99%) in H2O (200 mL). To this was added piperidine-3-carboxylic acid (25.8 g, 197.75 mmol, 1.00 equiv, 99%), in small portions at 0° C. Then, a solution of benzyl carbonochloridate (39.2 g, 227.48 mmol, 1.15 equiv, 99%) in Et2O (50 mL) was added at 0° C. over 40 minutes. Then a solution of NaOH (12 g, 1.50 equiv) in H2O (300 mL) was added drop wise with stirring at 0-10° C. The resulting solution was allowed to stir overnight at room temperature. The reaction progress was monitored by TLC (EtOAc/PE=1/1). The pH adjusted to 3 with 10% aqueous HCl. The resulting solution was extracted with ethyl acetate (3×500 mL). Combined organic layers were dried over anhydrous magnesium sulfate and concentrated on a rotary evaporator to afford 1-(benzyloxycarbonyl) piperidine-3-carboxylic acid (58 g) as white solid.

Step 2. Benzyl 3-(methoxy(methyl)carbamoyl)piperidine-1-carboxylate

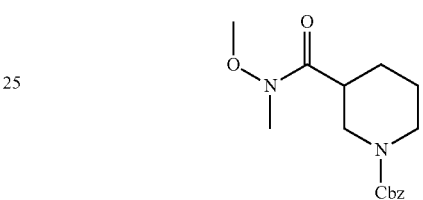

A 1000-mL 3-necked round-bottom flask was charged with a solution of N-methoxymethan amine hydrochloride (21.45 g, 217.7 mmol, 1.10 equiv, 99%) in dichloromethane (DCM) (250 mL). To the mixture was added Et3N (22.22 g, 217.80 mmol, 1.10 equiv, 99%) at 0-10° C., followed by addition 1-(benzyloxycarbonyl)piperidine-3-carboxylic acid (58 g, 220.3 mmol, 1.00 equiv) in dichloromethane (150 mL) drop wise at 2° C. over 2 hr period. To this mixture was added EDC.HCl (42.02 g, 217.80 mmol, 1.10 equiv, 99%) in several batches while maintaining the temperature below 5° C. The resulting solution was allowed to stir at room temperature overnight. The progress was monitored by TLC (EtOAc: PE=1:1). Upon completion, the reaction was then quenched by the addition of water (500 mL). The resulting mixture was then extracted with dichloromethane (2×500 mL). Combined organic layers were dried over anhydrous magnesium sulfate and concentrated on a rotary evaporator. The resulting residue was purified by a silica gel column chromatography eluted with ethyl acetate/petroleum ether (1:10) affording benzyl 3-(methoxy(methyl)carbamoyl)piperidine-1-carboxylate as a white syrup (57 g, 83%).

Step 3. Benzyl 3-acetylpiperidine-1-carboxylate

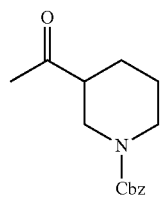

A 1000-mL 3-necked round-bottom flask was charged with a solution of MeMgBr (74.5 mL, 1.20 equiv, 3M in ether)

in Et₂O (200 mL). To this was added 3-(methoxy(methyl) carbamoyl)piperidine-1-carboxylate (57 g, 182.3 mmol, 1.00 equiv, 98%) in Et₂O (200 mL) at 0-5° C. over 1 hour. The resulting solution was allowed to stir for 1 hour at 0° C. and then warmed up to room temperature overnight. The progress was monitored by TLC (EtOAc/PE=1:1). Upon completion, the reaction was then quenched by the addition of 500 mL of saturated aqueous NH₄Cl. The mixture was then extracted with ethyl acetate (2×400 mL). Combined organic layers were then dried over anhydrous magnesium sulfate. The mixture was concentrated on a rotary evaporator to afford benzyl 3-acetylpiperidine-1-carboxylate as pale yellow syrup (32.8 g, 68%).

Step 4. (E)-Benzyl 3-(3-(dimethylamino)acryloyl) piperidine-1-carboxylate

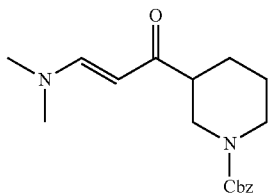

A 250-mL round-bottom flask was charged with a solution of benzyl 3-acetylpiperidine-1-carboxylate (15 g, 54.53 mmol, 1.00 equiv, 95%) in DMF (100 mL). To the mixture was added DMF-DMA (17 g, 141.43 mmol, 2.50 equiv, 99%). The resulting solution was allowed to reflux for about 6 hours. The mixture was then cooled down to room temperature and concentrated on a rotary evaporator affording crude (E)-benzyl 3-(3-(dimethylamino)acryloyl)piperidine-1-carboxylate as brown oil (19 g).

Step 5. Benzyl 3-(1H-pyrazol-5-yl)piperidine-1-carboxylate

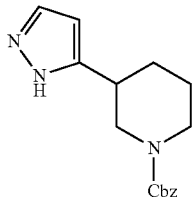

A 250-mL round-bottom flask was charged with a solution of (E)-benzyl 3-(3-(dimethylamino)acryloyl)piperidine-1-carboxylate (19 g, 54.05 mmol, 1.00 equiv, 90%) in ethanol (100 mL). To this was added conc.HCl (3 mL, 36%) drop wise and allowed to stir for 10 minutes. Then, to the resulting mixture was added NH₂NH₂.H₂O (60 mL, 80%) and refluxed overnight. The progress was monitored by TLC (EtOAc: PE=1:1). Upon completion, the resulting mixture was concentrated on a rotary evaporator and diluted with H₂O (200 mL). The mixture was extracted with ethyl acetate (3×200 mL). Combined organic layers were dried over anhydrous magnesium sulfate, filtered off and concentrated on a rotary evaporator affording a residue that was purified by a silica gel column chromatography eluted with ethyl acetate/petroleum ether (2:3) to give benzyl 3-(1H-pyrazol-5-yl)piperidine-1-carboxylate as colorless oil (13 g, 80%).

Step 6. 3-(1H-pyrazol-5-yl)piperidine

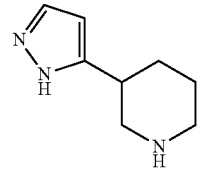

A 250-mL round-bottom flask was charged with a solution of benzyl 3-(1H-pyrazol-5-yl)piperidine-1-carboxylate (14 g, 46.61 mmol, 1.00 equiv, 95%) in dioxane (100 mL). To the mixture was added conc.HCl (60 mL, 36%). The resulting mixture was refluxed for 2 hours. The progress was monitored by TLC (DCM:MeOH=10:1). Upon completion, the resulting mixture was concentrated on a rotary evaporator. Then, pH was adjusted to 9 with saturated aqueous Na₂CO₃. The resulting mixture was then extracted with THF (8×200 mL). Combined organic layers were dried over anhydrous magnesium sulfate. After filtration and concentration on a rotary evaporator, the residue was purified by a silica gel column chromatography eluted with EtOAc/MeOH (10:1) affording 3-(1H-pyrazol-5-yl)piperidine as pale yellow oil (4 g, 54%). LCMS: [M+H]⁺: 152.1; ¹H NMR (CDCl₃) δ 7.47 (s, 1H), 6.05 (s, 1H), 3.16 (m, 1H), 3.11 (m, 2H), 2.99 (m, 1H), 2.76 (m, 1H), 2.57 (m, 2H), 1.95 (m, 1H), 1.56 (m, 1H), 1.46 (m, 2H).

Step 7. 3-((3-(1H-pyrazol-5-yl)piperidin-1-yl)methyl)-9-ethyl-9H-carbazole

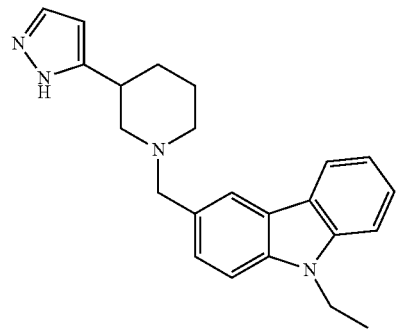

A 100-mL 3-necked round-bottom flask was charged with a solution of 3-(1H-pyrazol-5-yl)piperidine (1.8 g, 11.31 mmol, 1.00 equiv, 95%) in tetrahydrofuran (THF) (100 mL). To this was added 9-ethyl-9H-carbazole-2-carbaldehyde (2.66 g, 11.32 mmol, 1.02 equiv, 95%) and Ti(OiPr)₄ (4.24 g, 14.76 mmol, 1.25 equiv, 99%). The resulting solution was allowed to stir at room temperature overnight. To the mixture was then added NaBH₃CN (3 g, 47.26 mmol, 4.00 equiv, 99%). The resulting mixture was allowed to stir at room temperature overnight. The progress was monitored by TLC (DCM; MeOH=10:1). Upon completion, the reaction was quenched by the addition of saturated aqueous Na₂CO₃ (150 mL). The resulting mixture was extracted with ethyl acetate (5×200 mL). Combined organic layers were dried over MgSO₄, filtered off and concentrated on a rotary evaporator to give a residue that was purified by silica gel column chromatography eluted with DCM/MeOH (50:1) affording 3-((3-(1H-pyrazol-5-yl)piperidin-1-yl)methyl)-9-ethyl-9H-carbazole as a white solid (0.211 g, 5%). LCMS: [M+H]⁺: 359.2. ¹H NMR (CDCl₃,300 MHz) δ 8.11 (m, 1H), 8.00 (s, 1H), 7.48-7.36 (m, 5H), 7.24 (m, 1H), 6.03 (s, 1H), 4.37 (m, 2H), 3.93 (br, 2H), 3.76 (s, 2H), 3.15-2.60 (m, 5H), 1.67-1.56 (m, 4H), 1.43 (t, 3H).

EXAMPLE 2

4-((9-Ethyl-9H-carbazol-3-yl)methyl)morpholine

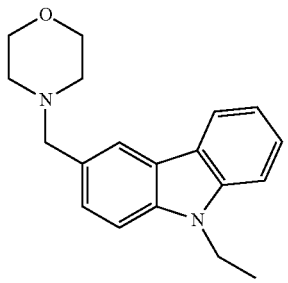

4-((9-Ethyl-9H-carbazol-3-yl)methyl)morpholine was prepared as described in Example 1. Morpholine was replaced for 3-(1H-pyrazol-5-yl)piperidine in Step 7 of Example 1. LCMS: [M+H]$^+$: 295.

EXAMPLE 3

1-((9-Ethyl-9H-carbazol-3-yl)methyl)piperidin-4-ol

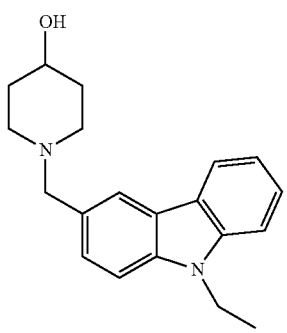

1-((9-Ethyl-9H-carbazol-3-yl)methyl)piperidin-4-ol was prepared as described in Example 1. Piperidin-4-ol was replaced for 3-(1H-pyrazol-5-yl)piperidine in Step 7 of Example 1. LCMS: [M+H]$^+$: 309

EXAMPLE 4

3-((3,5-Dimethylpiperidin-1-yl)methyl)-9-ethyl-9H-carbazole

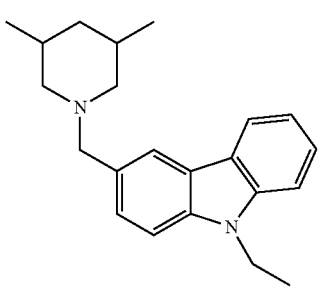

3-((3,5-Dimethylpiperidin-1-yl)methyl)-9-ethyl-9H-carbazole was prepared as described in Example 1. 3,5-dimethylpiperidine was replaced for 3-(1H-pyrazol-5-yl)piperidine in Step 7 of Example 1. LCMS: [M+H]$^+$: 321.

EXAMPLE 5

9-Ethyl-3-((4-methylpiperidin-1-yl)methyl)-9H-carbazole

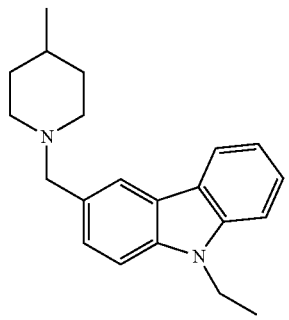

9-Ethyl-3-((4-methylpiperidin-1-yl)methyl)-9H-carbazole was prepared as described in Example 1. 4-methylpiperidine was replaced for 3-(1H-pyrazol-5-yl)piperidine in Step 7 of Example 1. LCMS: [M+H]$^+$: 307.

EXAMPLE 6

9-Ethyl-3-((3-methylpiperidin-1-yl)methyl)-9H-carbazole

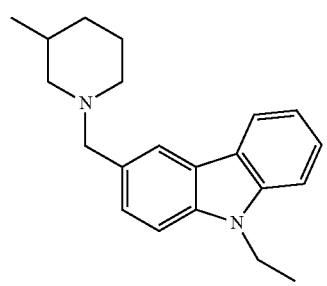

9-Ethyl-3-((3-methylpiperidin-1-yl)methyl)-9H-carbazole was prepared as described in Example 1. 3-methylpiperidine was replaced for 3-(1H-pyrazol-5-yl)piperidine in Step 7 of Example 1. LCMS: [M+H]$^+$: 307.

EXAMPLE 7

Ethyl 1-((9-ethyl-9H-carbazol-3-yl)methyl)piperidine-3-carboxylate

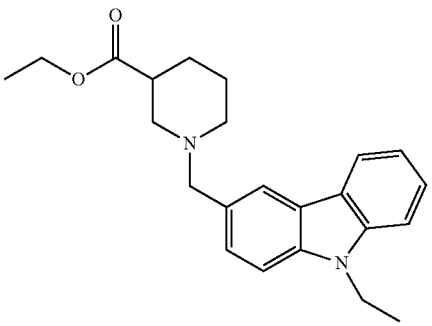

Ethyl 1-((9-ethyl-9H-carbazol-3-yl)methyl)piperidine-3-carboxylate was prepared as described in Example 1. Ethyl piperidine-3-carboxylate was replaced for 3-(1H-pyrazol-5-yl)piperidine in Step 7 of Example 1. LCMS: [M+H]$^+$: 365.

EXAMPLE 8

9-Ethyl-3-(pyrrolidin-1-ylmethyl)-9H-carbazole

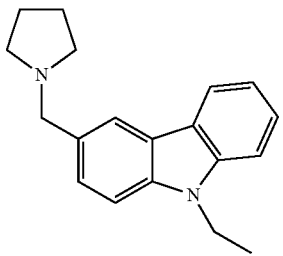

9-Ethyl-3-(pyrrolidin-1-ylmethyl)-9H-carbazole was prepared as described in Example 1. Pyrrolidine was replaced for 3-(1H-pyrazol-5-yl)piperidine in Step 7 of Example 1. LCMS: [M+H]$^+$: 279.

EXAMPLE 9

9-Ethyl-3-(piperazin-1-ylmethyl)-9H-carbazole

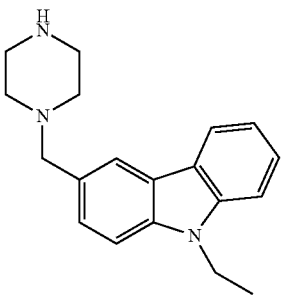

9-Ethyl-3-(piperazin-1-ylmethyl)-9H-carbazole was prepared as described in Example 1. Piperazine was replaced for 3-(1H-pyrazol-5-yl)piperidine in Step 7 of Example 1. LCMS: [M+H]$^+$: 294

EXAMPLE 10

1-((9-Ethyl-9H-carbazol-3-yl)methyl)piperidine-3-carboxamide

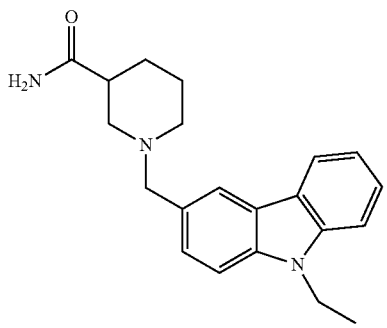

1-((9-Ethyl-9H-carbazol-3-yl)methyl)piperidine-3-carboxamide was prepared as described in Example 1. Piperidine-3-carboxamide was replaced for 3-(1H-pyrazol-5-yl)piperidine in Step 7 of Example 1. LCMS: [M+H]$^+$: 336. $^1$H NMR (DMSO-d$_6$, 300 MHz) δ 8.14 (d, 1H), 8.03 (s, 1H), 7.61-7.17 (m, 6H), 6.74 (s, 1H), 4.43 (m, 2H), 3.57 (m, 2H), 2.85-2.77 (m, 2H), 2.32-2.29 (m, 1H), 2.06-1.97 (m, 2H), 1.76-1.72 (m, 2H), 1.48-1.40 (m, 2H), 1.32 (t, 3H).

EXAMPLE 11

1-((9-Ethyl-9H-carbazol-3-yl)methyl)piperidine-3-carboxylic acid

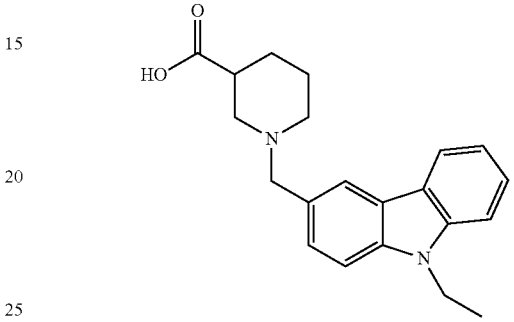

1-((9-Ethyl-9H-carbazol-3-yl)methyl)piperidine-3-carboxylic acid was prepared as described in Example 1. Piperidine-3-carboxylic acid was replaced for 3-(1H-pyrazol-5-yl) piperidine in Step 7 of Example 1. LCMS: [M+H]$^+$: 337. $^1$H NMR (CDCl$_3$, 300 MHz) δ 8.11-8.03 (m, 2H), 7.50-7.44 (m, 5H), 7.29-7.25 (m, 1H), 4.35 (m, 2H), 3.98 (m, 2H), 3.15-3.32 (m, 2H), 2.77 (s, 1H), 2.46-2.41 (m, 2H), 2.07-1.91 (m, 2H), 1.72 (br, 2H), 1.28 (t, 3H).

EXAMPLE 12

(1-((9-Ethyl-9H-carbazol-3-yl)methyl)piperidin-3-yl)methanol

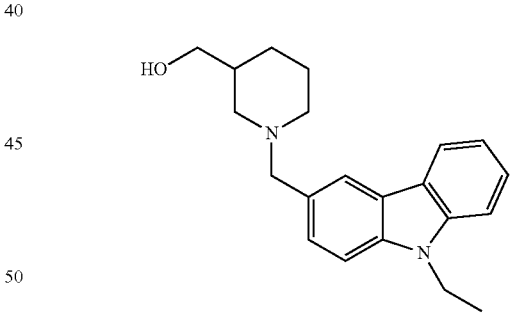

A 50-mL round-bottom flask was charged with a solution of ethyl 14(9-ethyl-9H-carbazol-3-yl)methyl)piperidine-3-carboxylate (300 mg, 0.82 mmol, 1.00 equiv) in THF (10 mL). To the mixture was added LiAlH$_4$ (130 mg, 2.06 mmol, 4.00 equiv) at 0° C. The resulting solution was stirred for 40 minutes at room temperature. The progress was monitored by TLC (dichloromethane/methanol=10:1). Upon completion, the reaction was then quenched by the addition of water (0.13 mL), 0.5 mL of NaOH/H$_2$O (15%). The solids were filtered out. The resulting mixture was concentrated on a rotary evaporator. The residue was purified by silica gel column chromatography eluted with dichloromethane/methanol (30:1) affording (14(9-ethyl-9H-carbazol-3-yl)methyl)piperidin-3-yl)methanol as brown solid (68 mg, 26%). LCMS: [M+H]$^+$: 323. $^1$H NMR (CDCl$_3$, 300 MHz) δ 8.11 (d, 1H), 8.04 (s, 1H), 7.51-7.37 (m, 5H), 7.27-7.22 (m, 1H), 4.37 (q, 2H), 3.76 (m, 1H), 3.65 (m, 1H), 5.56 (m, 1H), 2.88 (m, 1H), 2.69 (m, 1H), 2.26 (m, 2H), 1.90-1.65 (m, 4H), 1.44 (t, 3H), 1.24 (m, 1H).

EXAMPLE 13

1-((9-Ethyl-9H-carbazol-3-yl)methyl)piperidine-3-carbonitrile

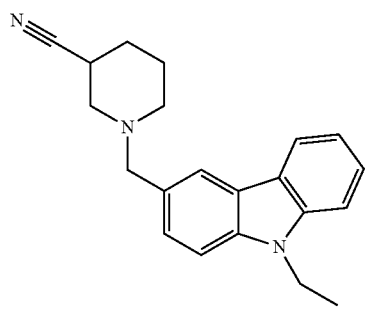

Step 1.
1-(Tert-butoxycarbonyl)piperidine-3-carboxylic acid

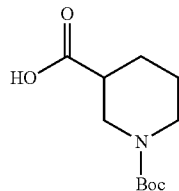

A 250-mL 3-necked round-bottomed flask was charged with a solution of piperidine-3-carboxylic acid (4.0 g, 30.39 mmol, 1.00 equiv, 98%) in EtOH (70 mL), tert-butoxycarbonyl (8.2 g, 36.86 mmol, 1.21 equiv, 98%) and $K_2CO_3$ (4.3 g, 30.54 mmol, 1.00 equiv, 98%). The resulting mixture was stirred overnight at room temperature overnight. Then, the mixture was diluted with water. The pH was adjusted to 3 with aqueous 10% HCl resulting in a precipitate. The mixture was then filtered to collect solids that were washed with water and dried in a vacuum oven under reduced pressure to afford 1-(tert-butoxycarbonyl)piperidine-3-carboxylic acid as white solid (8.7 g).

Step 2. Tert-butyl 3-carbamoylpiperidine-1-carboxylate

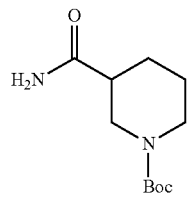

A 1-L 3-necked round-bottomed flask was charged with a solution of 1-(tert-butoxycarbonyl)piperidine-3-carboxylic acid (10 g, 42.79 mmol, 1.00 equiv, 98%), TEA (5.2 g, 50.46 mmol, 1.18 equiv, 98%) in THF (100 mL). To this mixture was added isobutyl carbonochloridate (6.8 g, 49.00 mmol, 1.15 equiv, 98%) drop wise at 10° C. The resulting solution was stirred for 15 minutes at 10° C. in a water/ice bath. Then, to the mixture was added $NH_3.H_2O$ (25%, 60 mL) and allowed to stir for 10 minutes at 10° C. Then, it was treated with water (40 mL) to afford off-white solids after filtration. The solid was dried in an oven under reduced pressure affording tert-butyl 3-carbamoylpiperidine-1-carboxylate as white solid (7 g, 72%).

Step 3. Tert-butyl 3-cyanopiperidine-1-carboxylate

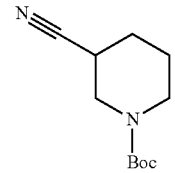

A 250-mL 3-necked round-bottomed flask was charged with a solution of tert-butyl 3-carbamoylpiperidine-1-carboxylate (5 g, 21.49 mmol, 1.00 equiv, 98%) in pyridine (50 mL). To this solution, $POCl_3$ (5 g, 32.24 mmol, 1.50 equiv, 98%) was added drop wise at 0° C. and allowed to stir at 0° C. for 1 hour. The progress was monitored by TLC (EA:PE=1:1). The pyridine was removed by distillation. The mixture was diluted with $H_2O$ (40 mL) and pH was adjusted to 8 by addition of aqueous $NaHCO_3$. Then, the resulting mixture was extracted with ethyl acetate (3×30 mL). Combined organic layers were dried over anhydrous sodium sulfate, filtered off and concentrated on a rotary evaporator. The crude was purified by distillation under reduced pressure (30 mm Hg) and the fractions collected at 40° C. to afford tert-butyl 3-cyanopiperidine-1-carboxylate as yellow oil (2.6 g, 53%).

Step 4. Piperidine-3-carbonitrile hydrochloride

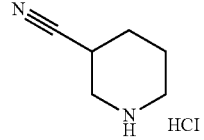

A 250-mL 3-necked round-bottomed flask was charged with tert-butyl 3-cyanopiperidine-1-carboxylate (5.8 g, 27.07 mmol, 1.00 equiv, 98%) in 1,4-dioxane (60 mL). The mixture was cooled down to at 0° C. and treated with HCl (g). The mixture was stirred for 2 hours at 0° C. resulting in a precipitate that was collected by filtration to afford piperidine-3-carbonitrile hydrochloride as white solid (1.9 g, 48%).

Step 5. 1-((9-Ethyl-9H-carbazol-3-yl)methyl)piperidine-3-carbonitrile

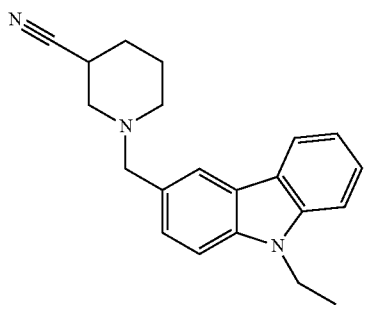

1-((9-Ethyl-9H-carbazol-3-yl)methyl)piperidine-3-carbonitrile was prepared as described in Example 1. Piperidine-3-carbonitrile hydrochloride was replaced for 3-(1H-pyrazol-5-yl)piperidine in Step 7 of Example 1. LCMS: [M+H]$^+$: 318. $^1$H NMR (DMSO-d$_{63}$, 300 MHz) δ 8.14-8.11 (m, 2H), 7.61-7.55 (m, 2H), 7.47-7.40 (m, 2H), 7.21-7.16 (m, 1H), 4.48-4.41 (m, 2H), 3.75-3.62 (m, 2H), 3.01 (br, 1H), 2.62-2.37 (m, 4H), 1.76-1.56 (m, 4H), 1.32 (t, 3H).

EXAMPLE 14

3-((3-(1H-tetrazol-5-yl)piperidin-1-yl)methyl)-9-ethyl-9H-carbazole

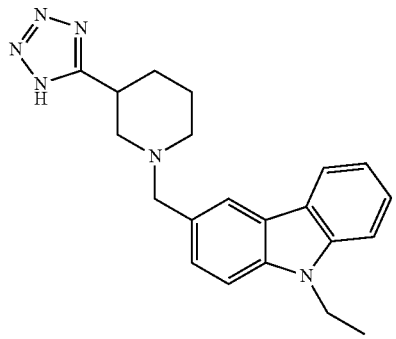

A 100-mL 3-necked round-bottomed flask was charged with a solution of 1-((9-Ethyl-9H-carbazol-3-yl)methyl)piperidine-3-carbonitrile (700 mg, 2.17 mmol, 1.00 equiv, 98%) in toluene (30 mL). To this solution was add AlMe$_3$ (960 mg, 13.07 mmol, 6.02 equiv, 98%) and TMSN$_3$ (1.52 g, 12.95 mmol, 5.97 equiv, 98%). The resulting mixture was stirred at 80° C. overnight. Upon completion, it was cooled down to room temperature and transferred into a reparatory funnel and extracted with ethyl acetate (3×50 mL). Combined organic layers were with brine and aqueous NaHCO$_3$ (10%). The mixture was dried over anhydrous magnesium sulfate, filtered and concentrated to give the crude that was purified by preparative HPLC eluted with 1-10% MeOH in DCM affording 3-((3-(1H-tetrazol-5-yl)piperidin-1-yl)methyl)-9-ethyl-9H-carbazole as white solid (85 mg, 16%). LCMS: [M+H]$^+$: 361. $^1$H NMR (DMSO-d$_{63}$, 300 MHz) δ 8.15-8.10 (m, 2H), 7.62-7.57 (m, 2H), 7.47-7.43 (m, 2H), 7.22-7.18 (m, 1H), 4.47-4.40 (m, 2H), 3.92-3.82 (m, 2H), 3.26-3.16 (m, 2H), 2.98-2.94 (m, 1H), 2.37-2.31 (m, 1H), 2.04-2.00 (m, 1H), 1.74-1.57 (m, 3H), 1.32 (t, 3H).

SCHEME 2

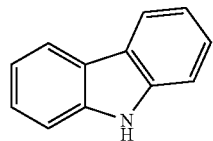

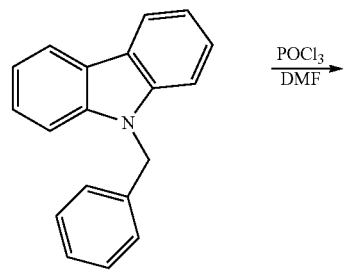

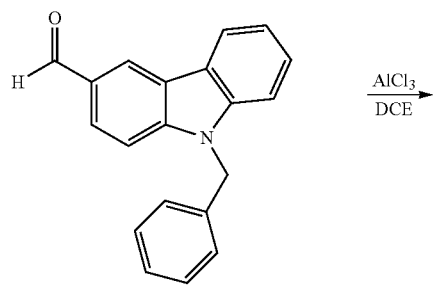

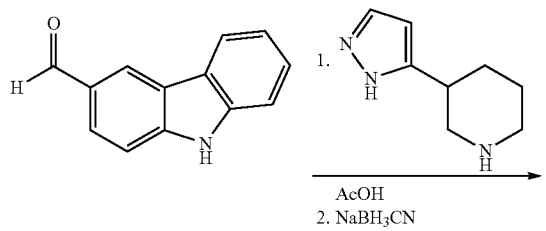

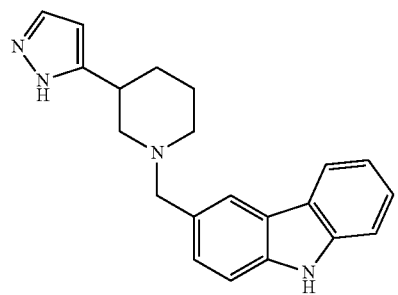

EXAMPLE 15

3-((3-(1H-pyrazol-5-yl)piperidin-1-yl)methyl)-9H-carbazole

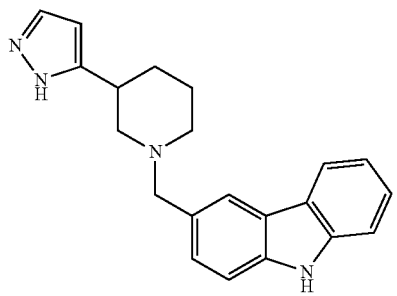

Step 1. 9-Benzyl-9H-carbazole

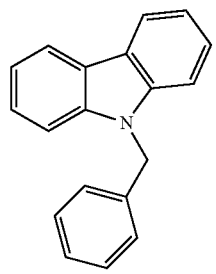

A 100-mL round-bottomed flask was charged with a solution of 9H-carbazole (1.67 g, 9.90 mmol, 1.00 equiv, 99%) in DMF (20 mL) followed by addition of NaH (400 mg, 16.50 mmol, 1.00 equiv, 99%) in small portions at 0° C. over 5 minutes. 1-(Bromomethyl)benzene (1.7 g, 9.90 mmol, 1.00 equiv, 99%) was then added drop wise at 0° C. over 5 minutes. The resulting mixture was stirred at room temperature for 16 hours. The progress was monitored by TLC (EtOAc:PE=1:5). Upon completion, the reaction was then quenched by the addition of water/ice (100 mL). The solids were collected by filtration and dried in an oven under reduced pressure to afford 9-benzyl-9H-carbazole as white solid (2.3 g, 90%). LCMS: [M+H]$^+$: 258.

Step 2. 9-Benzyl-9H-carbazole-3-carbaldehyde

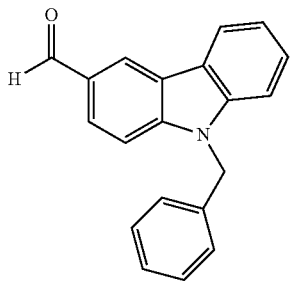

A 50-mL 3-necked round-bottomed flask was charged with N,N-dimethylformamide (400 mg, 5.42 mmol, 2.80 equiv, 99%). To this, POCl$_3$ (700 mg, 4.56 mmol, 2.40 equiv, 99%) was added drop wise with stirring at 0° C. and allowed to stir at room temperature for 1 hour. To this mixture was added 9-benzyl-9H-carbazole (500 mg, 1.93 mmol, 1.00 equiv, 99%) in small portions at 45° C. over 5 minutes. Then, the temperature was raised to 95° C. in an oil bath and allowed to stir for 18 hours. The progress was monitored by TLC (EtOAc:PE=1:4). Upon completion, the reaction mixture was cooled down to room temperature and quenched with water (20 mL). The resulting mixture was allowed to stir for an additional 4 hours at room temperature. The solids were collected by filtration and dried to afford 9-benzyl-9H-carbazole-3-carbaldehyde as green solid (200 mg, 36.1%). LCMS: [M+H]$^+$: 286

Step 3. 9H-Carbazole-3-carbaldehyde

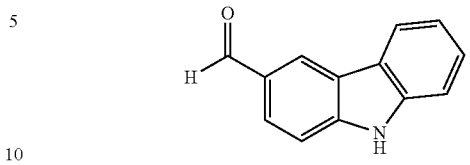

A 250-mL round-bottomed flask was charged with a solution of AlCl$_3$ (9.26 g, 69.45 mmol, 20.00 equiv, 99%) in 1,2-dichloroethane (150 mL). To this was added 9-benzyl-9H-carbazole-3-carbaldehyde (1 g, 3.47 mmol, 1.00 equiv, 99%) in several batches at room temperature over 5 minutes. The resulting mixture was stirred for 2 hours at room temperature. The reaction was then quenched by the addition of H$_2$O/ice (100 mL). The solids were filtered out. The resulting solution was extracted with DCM (3×100 mL) and the combined organic layers were concentrated on a rotary evaporator to give a residue that was purified by silica gel column chromatography eluted with PE:EtOAc (10:1) to afford 9H-carbazole-3-carbaldehyde as green solid (270 mg, 40%). LCMS: [M+H]$^+$: 196

Step 4. 3-((3-(1H-Pyrazol-5-yl)piperidin-1-yl)methyl)-9H-carbazole

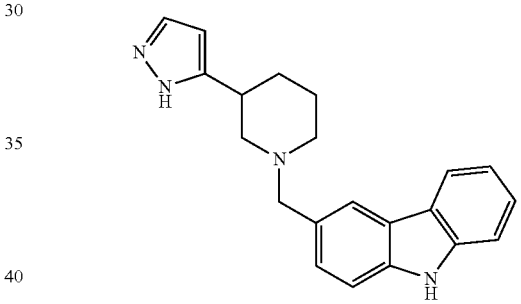

A 50-mL 3-necked round-bottomed flask was charged with a solution of 4-(1H-pyrazol-5-yl)piperidine (412 mg, 1.83 mmol, 1.50 equiv, 99%) in EtOH (10 mL). To this was added N-ethyl-N-isopropylpropan-2-amine (639 mg, 4.90 mmol, 4.00 equiv, 99%). After stirring for 30 minutes, 9H-carbazole-3-carbaldehyde (240 mg, 1.22 mmol, 1.00 equiv, 99%) was added followed by acetic acid (221 mg, 3.65 mmol, 3.00 equiv, 99%). The mixture was allowed to stir for 30 minutes at room temperature. To the mixture was then added NaBH$_3$CN (156 mg, 2.45 mmol, 2.00 equiv, 99%). The resulting mixture was stirred for 16 hours at 40° C. in an oil bath. The reaction progress was monitored by TLC (DCM:MeOH=5:1). Upon completion, the mixture was diluted with H$_2$O (20 mL) and, pH was adjusted to 8 with NaHCO$_3$ (1 M). Then, the resulting solution was extracted with ethyl acetate (5×20 mL). The combined organic layers were dried over anhydrous sodium sulfate and concentrated to give a residue that was purified with silica gel column chromatography eluted with dichloromethane/methanol (20:1) affording 3-((3-(1H-pyrazol-5-yl)piperidin-1-yl)methyl)-9H-carbazole as white solid (38 mg, 9%). LCMS: [M+H]$^+$: 331. $^1$H NMR (DMSO-d$_6$, 300 MHz) δ 12.42 (s, 1H), 11.20 (s, 1H), 8.11-8.09 (d, 1H), 8.00 (s, 1H), 7.48-7.33 (m, 4H), 7.11-7.16 (m, 1H), 6.03 (s, 1H), 3.64 (s, 2H), 3.01-2.98 (d, 1H), 2.86-2.82 (s, 2H), 2.09-1.90 (m, 3H), 1.67-1.57 (m, 2H), 1.41-1.37 (m, 1H).

EXAMPLE 16

1-((9-ethyl-9H-carbazol-3-yl)methyl)-N-methylpiperidine-3-carboxamide

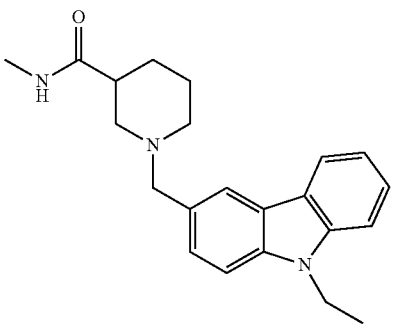

A 50-mL seal tube charge with a solution of ethyl 1-((9-ethyl-9H-carbazol-3-yl)methyl)piperidine-3-carboxylate (500 mg, 1.37 mmol, 1.00 equiv) in $CH_3NH_2$ (25 mL). To the mixture was added $CuSO_4$ (100 mg, 0.51 mmol, 0.37 equiv). The resulting solution was stirred at 140° C. for 24 hours in an oil bath. The progress was monitored by TLC (dichloromethane/methanol=5:1). Upon completion, the solids were filtered out. The resulting solution was extracted with dichloromethane (2×50 mL). The combined organic layers were dried over anhydrous sodium sulfate and concentrated on a rotary evaporator. The residue was purified by silica gel column chromatography eluted with dichloromethane/methanol (30:1) affording 1-((9-ethyl-9H-carbazol-3-yl)methyl)-N-methylpiperidine-3-carboxamide as white solid (28 mg, 6%). LCMS: $[M+H]^+$: 350. $^1H$ NMR ($CDCl_3$, 300 MHz) δ 8.10 (d, 1H), 8.01 (s, 1H), 7.53-7.39 (m, 4H), 7.29-7.24 (m, 1H), 4.44-4.37 (q, 2H), 3.85-3.81 (d, 1H), 3.69-3.65 (d, 1H), 2.89 (m, 2H), 2.80-2.78 (d, 3H), 2.59 (br, 1H), 2.45 (br, 2H), 1.91 (m, 1H), 1.73-1.73 (m, 3H), 1.47 (t, 3H).

EXAMPLE 17

3-((3-(1H-imidazol-2-yl)piperidin-1-yl)methyl)-9-ethyl-9H-carbazole

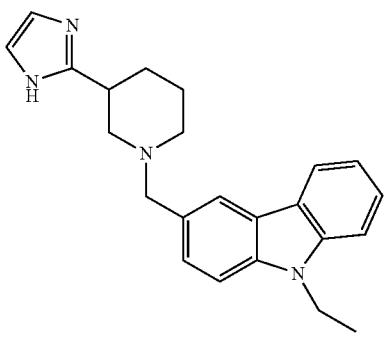

Step 1. 1-Benzyl 3-ethyl piperidine-1,3-dicarboxylate

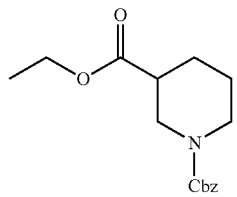

A 250-mL round-bottomed flask was charged with a solution of $NaHCO_3$ (10.7 g, 127.38 mmol, 2.00 equiv) in $H_2O$ (80 mL), ethyl piperidine-3-carboxylate (10 g, 63.69 mmol, 1.00 equiv) and benzyl carbonochloridate (11.9 g, 70.00 mmol, 1.10 equiv). The resulting solution was stirred for 16 hours at room temperature. The progress was monitored by TLC (EtOAc: PE=1:5). Upon completion, the resulting solution was extracted with ethyl acetate (3×50 mL). Combined organic layers were dried over anhydrous sodium sulfate. The solids were filtered out. The resulting mixture was concentrated on a rotary evaporator. The residue was purified by a silica gel column chromatography eluted with ethyl acetate/petroleum ether (1:100) afford 1-benzyl 3-ethyl piperidine-1,3-dicarboxylate as pale yellow oil (11.4 g, (62%).

Step 2. Benzyl 3-(hydroxymethyl)piperidine-1-carboxylate

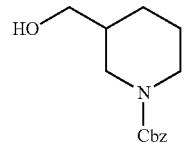

A 250-mL 3-necked round-bottomed flask was charged with a solution of $LiAlH_4$ (2.96 g, 77.83 mmol, 2.00 equiv) in THF (150 mL). To this solution was added 1-benzyl 3-ethyl piperidine-1,3-dicarboxylate (11.4 g, 39.16 mmol, 1.00 equiv) in THF (50 mL) drop wise with stirring at −10° C. The resulting mixture was allowed to stir about 1 hour at −10° C. The progress was monitored by TLC (DCM: MeOH=10:1). The resulting solution was diluted with 10 mL of $NaOH/H_2O$. The solids were filtered out. The resulting mixture was concentrated on a rotary evaporator to afford benzyl 3-(hydroxymethyl)piperidine-1-carboxylate as pale yellow oil in (8.94 g, (92%).

Step 3. Benzyl 3-formylpiperidine-1-carboxylate

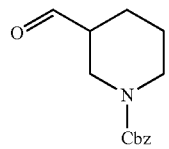

A 500-mL round-bottomed flask was charged a solution of benzyl 3-(hydroxymethyl)piperidine-1-carboxylate (8.94 g, 35.90 mmol, 1.00 equiv) in DCM (200 mL), $NaHCO_3$ (9.05 g, 107.74 mmol, 3.00 equiv) in H₂O (80 mL), I₂ (18.24 g, 71.81 mmol, 2.00 equiv) and TEMPO (570 mg, 3.65 mmol, 0.10 equiv). The resulting mixture was stirred for 18 hours at room temperature. The reaction progress was monitored by TLC (DCM:MeOH=20:1). Upon completion, the reaction was then quenched by the addition of 10 mL of NaHSO₃/H₂O. The pH was adjusted to 8 with NaHCO₃. The resulting solution was extracted with dichloromethane (3×50 mL). Combined organic layers were dried over anhydrous sodium sulfate, filtered off and concentrated on a rotary evaporator to afford benzyl 3-formylpiperidine-1-carboxylate as brown oil (6.2 g, (70%).

Step 4. Benzyl 3-(1H-imidazol-2-yl)piperidine-1-carboxylate

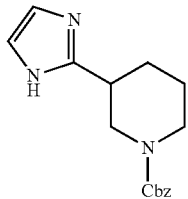

A 250-mL round-bottomed flask was charged with a solution of benzyl 3-formylpiperidine-1-carboxylate (1 g, 4.05 mmol, 1.00 equiv) in EtOH (60 mL) and oxalaldehyde (20 mL). To the mixture was added NH₃.H₂O (20 mL). The resulting mixture was stirred for 16 hours at room temperature. The progress was monitored by TLC (DCM:MeOH=10:1). Upon completion, the resulting mixture was diluted with H₂O (50 mL). The resulting solution was extracted with dichloromethane (3×50 mL) and the combined organic layers were dried over anhydrous sodium sulfate. The solids were filtered out. The resulting mixture was concentrated on a rotary evaporator affording benzyl 3-(1H-imidazol-2-yl)piperidine-1-carboxylate as a pale yellow solid (0.3 g, 26%).

Step 5. 3-(1H-Imidazol-2-yl)piperidine hydrochloride

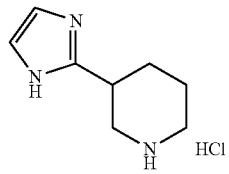

A 250-mL round-bottomed flask was charged with a solution of benzyl 3-(1H-imidazol-2-yl)piperidine-1-carboxylate (1.5 g, 5.26 mmol, 1.00 equiv) in dioxane (15 mL). To this was added conc. HCl (9 mL). The resulting mixture was stirred for 4 hours at 70° C. in an oil bath. The reaction progress was monitored by TLC (DCM: MeOH=10:1). Upon completion, the resulting solution was diluted with dioxane (10 mL) and concentrated on a rotary evaporator affording 3-(1H-imidazol-2-yl)piperidine hydrochloride as black solid in (0.48 g, 57%).

Step 6. 3-((3-(1H-Imidazol-2-yl)piperidin-1-yl)methyl)-9-ethyl-9H-carbazole

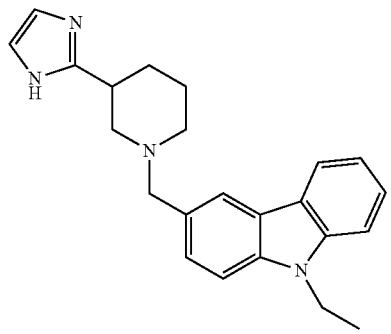

3-((3-(1H-Imidazol-2-yl)piperidin-1-yl)methyl)-9-ethyl-9H-carbazole was prepared as described in Example 1. 3-(1H-imidazol-2-yl)piperidine hydrochloride was replaced for 3-(1H-pyrazol-5-yl)piperidine in Step 7 of Example 1. LCMS: [M+H]⁺: 359. ¹H NMR (DMSO-d₆, 300 MHz) δ 10.29 (br, 1H), 8.29 (s, 1H), 8.10 (d, 1H), 7.69 (m, 2H), 7.58 (m, 3H), 7.49 (t, 1H), 7.26 (t, 1H), 4.47 (m, 4H), 3.73 (br, 1H), 3.57 (br, 2H), 3.24 (br, 1H), 2.98 (br, 1H), 2.00 (m, 2H), 1.80 (m, 2H), 1.33 (t, 3H).

EXAMPLE 18

3-((3-(1H-1,2,3-triazol-1-yl)piperidin-1-yl)methyl)-9-ethyl-9H-carbazole

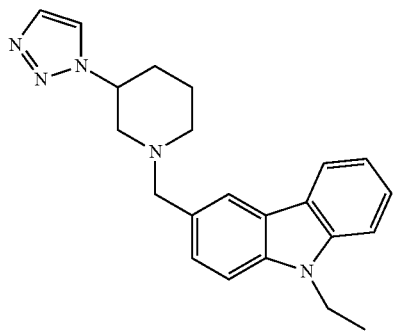

Step 1. tert-Butyl 3-(4-nitrophenylsulfonyloxy)piperidine-1-carboxylate

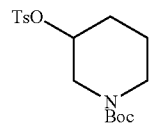

A 500-mL round-bottomed flask was charged with a solution of tert-butyl 3-hydroxypiperidine-1-carboxylate (16 g, 79.60 mmol, 1.00 equiv) in DCM (200 mL), 4-nitrobenzene-1-sulfonyl chloride (17.6 g, 79.64 mmol, 1.00 equiv) and pyridine (9 mL). The resulting solution was stirred at 40° C. for 16 hours. The reaction progress was monitored by TLC (EtOAc: PE=1:2). Upon completion, the reaction was then quenched by the addition of aqueous NaHCO₃ (200 mL). The resulting mixture was extracted with dichloromethane (4×100 mL). Combined organic layers were washed with brine (1×30 mL). The organic layers were dried over anhydrous sodium sulfate and concentrated on a rotary evaporator. The residue was purified by silica gel column chromatography eluted with ethyl acetate/petroleum ether (1:10-1:2) affording tert-butyl 3-(4-nitrophenylsulfonyloxy)piperidine-1-carboxylate as yellow solid (23 g, 75%).

Step 2. Tert-butyl 3-(1H-1,2,3-triazol-1-yl)piperidine-1-carboxylate

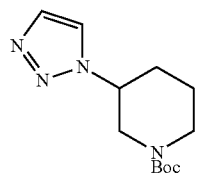

A 1000-mL 4-necked round-bottomed flask was charged with a solution of 2H-1,2,3-triazole (30 g, 434.78 mmol, 1.00 equiv) in benzene (500 mL). To this solution was added chlorotrimethylsilane (49.3 g, 456.48 mmol, 1.05 equiv) drop wise 0° C. followed by addition of triethylamine (48.3 g, 478.22 mmol, 1.10 equiv). The resulting solution was stirred for 16 hours at room temperature. The solids were filtered out. The resulting mixture was concentrated under vacuum. The crude product was purified by distillation and the fraction was collected at 140-150° C. affording 2-(trimethylsilyl)-2H-1,2,3-triazole as colorless oil (11 g, 18%). To a solution of 2-(trimethylsilyl)-2H-1,2,3-triazole (6.2 g, 43.97 mmol, 2.74 equiv) in DMF (100 mL) was added tert-butyl 3-(4-nitrophenylsulfonyloxy)piperidine-1-carboxylate (6.2 g, 16.06 mmol, 1.00 equiv). The resulting solution was refluxed for 3 hours. Upon completion, the mixture was cooled down to room temperature and concentrated on a rotary evaporator affording tert-butyl 3-(1H-1,2,3-triazol-1-yl)piperidine-1-carboxylate as brown solid (2.3 g).

Step 3. 3-(1H-1,2,3-Triazol-1-yl)piperidine hydrochloride

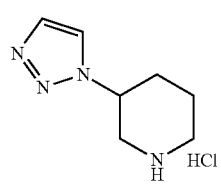

A 100-mL round-bottomed flask was charged with a solution of tert-butyl 3-(1H-1,2,3-triazol-1-yl)piperidine-1-carboxylate (2.8 g, 11.11 mmol, 1.00 equiv) in MeOH (50 mL). To this mixture was added conc. HCl (10 mL). The resulting solution was stirred at 30° C. for 5 hours in an oil bath. Upon completion, the resulting mixture was cooled down to room temperature and concentrated on a rotary evaporator affording 3-(1H-1,2,3-triazol-1-yl)piperidine hydrochloride as pale yellow solid (3 g).

Step 4. 3-((3-(1H-1,2,3-Triazol-1-yl)piperidin-1-yl)methyl)-9-ethyl-9H-carbazole

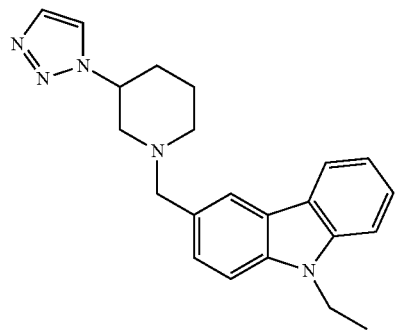

3-((3-(1H-1,2,3-Triazol-1-yl)piperidin-1-yl)methyl)-9-ethyl-9H-carbazole was prepared as described in Example 1. 3-(1H-1,2,3-Triazol-1-yl)piperidine hydrochloride was replaced for 3-(1H-pyrazol-5-yl)piperidine in Step 7 of Example 1. LCMS: [M+H]⁺: 360. ¹H NMR (DMSO-d₆, 300 MHz) δ 8.13 (d, 1H), 8.04 (s, 1H), 7.74 (s, 2H), 7.54 (m, 2H), 7.39 (m, 2H), 7.16 (t, 1H), 4.58 (m, 1H), 4.42 (m, 2H), 3.68 (m, 2H), 2.89 (d, 2H), 2.33 (m, 1H), 2.10 (m, 2H), 1.85 (m, 2H), 1.69 (m, 1H), 1.32 (t, 3H).

EXAMPLE 19

3-((3-(4H-1,2,4-Triazol-3-yl)piperidin-1-yl)methyl)-9-ethyl-9H-carbazole

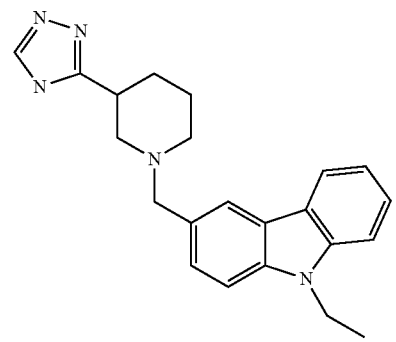

Step 1. Methyl 1-((9-ethyl-9H-carbazol-3-yl)methyl)piperidine-3-carbimidate hydrochloride

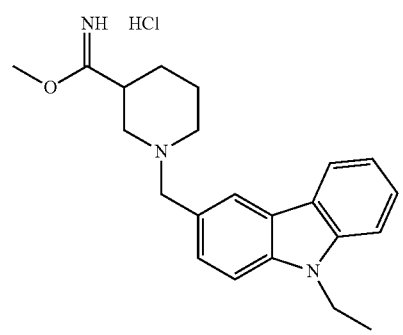

A 100-mL 3-necked round-bottomed flask was charged with 1-((9-ethyl-9H-carbazol-3-yl)methyl)piperidine-3-carbonitrile (1.31 g, 4.05 mmol, 1.00 equiv, 98%) from Example 13 in anhydrous MeOH (20 mL). Then, this was treated with HCl gas. The resulting solution was allowed to stir at −5° C. for 3 hours, followed by at −20° C. for overnight. Resulting precipitate was collected by filtration and dried to afford methyl 1-((9-ethyl-9H-carbazol-3-yl)methyl)piperidine-3-carbimidate hydrochloride as white solid (1.44 g, 92%).

Step 2. 3-((3-(4H-1,2,4-Triazol-3-yl)piperidin-1-yl)methyl)-9-ethyl-9H-carbazole

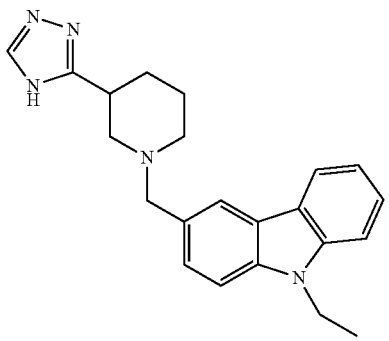

A 100-mL round-bottomed flask was charged with a solution of methyl 1-((9-ethyl-9H-carbazol-3-yl)methyl)piperidine-3-carbimidate hydrochloride (1.44 g, 3.94 mmol, 1.00 equiv, 1.44%) in pyridine (20 mL) and formohydrazide (0.249 g, 4.07 mmol, 1.03 equiv, 0.249%). The resulting solution was stirred overnight at 110° C. in an oil bath. Upon completion, the resulting solution was cooled down to room temperature and diluted with water. This mixture was then extracted with ethyl acetate (3×30 mL). Combined organic layers were dried over anhydrous sodium sulfate. After filtration, organic later was concentrated on a rotary evaporator to give a residue that was purified by a silica gel column chromatography eluted with ethyl acetate/hexane (1:10) affording 3-((3-(2H-1,2,4-triazol-3-yl)piperidin-1-yl)methyl)-9-ethyl-9H-carbazole as white solid (0.011 g, 1%). LCMS: [M+H]$^+$: 360. $^1$H NMR (CDCl$_3$, 300 MHz) δ 11.55 (s, 1H), 8.10 (m, 3H), 7.68 (d, 1H), 7.50 (t, 1H), 7.38 (m, 2H), 7.25 (t, 1H), 4.35 (t, 3H), 3.76 (d, 2H), 3.50 (d, 1H), 2.66 (s, 1H), 2.32 (d, 1H), 2.12 (d, 1H), 2.01 (d, 1H), 1.84 (d, 1H), 1.55 (d, 1H), 1.39 (t, 3H).

EXAMPLE 20

1-((9-ethyl-9H-carbazol-3-yl)methyl)-N,N-dimethylpiperidine-3-carboxamide

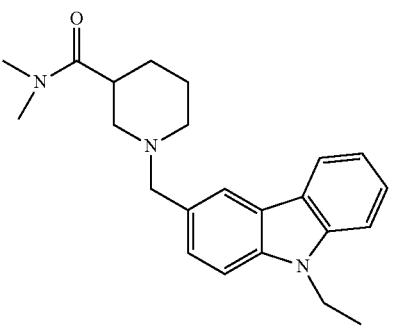

A 100-mL 3-necked round-bottomed flask was charged with a solution of 1-((9-ethyl-9H-carbazol-3-yl)methyl)piperidine-3-carboxylic acid (1 g, 2.98 mmol, 1.00 equiv) in DMF (50 mL), followed by HNMe$_2$.HCl (723 mg, 8.93 mmol, 3.00 equiv) and triethylamine (1.2 g, 11.88 mmol, 4.00 equiv) at 0° C. To this mixture was added HATU (1.13 g, 2.97 mmol, 1.00 equiv) at 0° C. The resulting mixture was stirred at room temperature for 16 hours. The reaction progress was monitored by TLC (DCM:MeOH=10:1). Upon completion, the resulting mixture was diluted with brine (30 mL) and extracted with ethyl acetate (3×50 mL). The combined organic layers were dried over anhydrous sodium sulfate, filtered off and concentrated on a rotary evaporator. The residue was purified by a silica gel column chromatography eluted with dichloromethane/methanol (100:1) affording 1-((9-ethyl-9H-carbazol-3-yl)methyl)-N,N-dimethylpiperidine-3-carboxamide as a white solid (0.8 g, 74%). LCMS: [M+H]$^+$: 364. $^1$H NMR (CDCl$_3$, 300 MHz) δ 8.17 (t, 2H), 7.44 (m, 4H), 7.30 (t, 1H), 4.35 (m, 4H), 3.28 (m, 4H), 3.06 (s, 3H), 2.94 (d, 3H), 2.35 (s, 2H), 1.85 (m, 3H), 1.42 (t, 3H).

EXAMPLE 21

3-((3-(1H-Imidazol-5-yl)piperidin-1-yl)methyl)-9-ethyl-9H-carbazolee

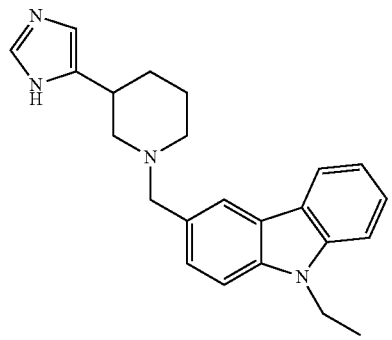

Step 1. Benzyl 3-(1H-imidazol-5-yl)piperidine-1-carboxylate

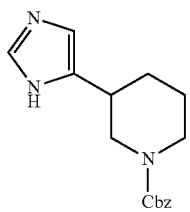

A 250-mL 3-necked round-bottomed flask was charged with a solution of benzyl 3-formylpiperidine-1-carboxylate (1 g, 4.05 mmol, 1.00 equiv) in toluene (80 mL), TsOH (0.5 g), 4-methylbenzenesulfonamide (1.39 g, 8.13 mmol, 2.00 equiv), K$_2$CO$_3$ (4.47 g, 32.39 mmol, 8.00 equiv), 1-(isocyanomethylsulfonyl)-4-methylbenzene (2.38 g, 12.21 mmol, 3.00 equiv) in MeOH (40 mL) and 1,2-dimethoxyethane (80 mL).

The resulting mixture was heated to 80° C. in an oil bath for 20 hours. The reaction progress was monitored by TLC (DCM: MeOH=10:1). After cooling to room temperature, the resulting mixture was concentrated on a rotary evaporator. The mixture was then diluted with water (80 mL) and extracted with dichloromethane (4×50 mL). The combined organic layers were dried over anhydrous sodium sulfate, filtered out and concentrated on a rotary evaporator. The residue was purified by silica gel column chromatography eluted with DCM/CH₃OH (50/1) affording benzyl 3-(1H-imidazol-5-yl)piperidine-1-carboxylate as brown oil (0.75 g, 65%).

Step 2. 3-(1H-Imidazol-5-yl)piperidine

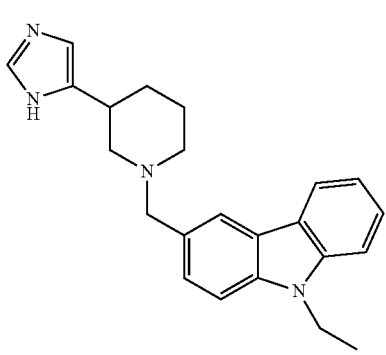

A 100-mL round-bottomed flask was charged with a solution of benzyl 3-(1H-imidazol-5-yl)piperidine-1-carboxylate (3 g, 10.53 mmol, 1.00 equiv) in 1,4-dioxane (30 mL) and conc. HCl (18 mL). The resulting mixture was heated to 80° C. in an oil bath for 16 hours. The reaction progress was monitored by TLC (DCM: MeOH=10:1). Upon completion, the resulting mixture was concentrated on a rotary evaporator. The resulting solution was diluted with water (60 mL) and treated with aqueous NaHCO₃. The resulting mixture was then extracted with dichloromethane (4×40 mL). The combined organic layers were dried over anhydrous sodium sulfate, filtered off and concentrated on a rotary evaporator affording 3-(1H-imidazol-5-yl)piperidine as brown oil (0.5 g, 31%).

Step 3. 3-((3-(1H-imidazol-5-yl)piperidin-1-yl)methyl)-9-ethyl-9H-carbazole 3-((3-(1H-imidazol-5-yl)piperidin-1-yl)methyl)-9-ethyl-9H-carbazole was prepared as described in Example 1. 3-(1H-Imidazol-5-yl)piperidine was replaced for 3-(1H-pyrazol-5-yl)piperidine in Step 7 of Example 1. LCMS: [M+H]⁺: 359. ¹H NMR (DMSO-d₆, 300 MHz) δ 10.08 (s, 1H), 9.01 (s, 1H), 8.30 (s, 1H), 8.11 (d, 1H), 7.66 (m, 2H), 7.58 (d, 2H), 7.49 (t, 1H), 7.23 (t, 1H), 4.48 (m, 4H), 3.54 (m, 2H), 3.09 (m, 3H), 2.03 (m, 2H), 1.80 (m, 1H), 1.58 (m, 1H), 1.30 (t, 3H).

SCHEME 3

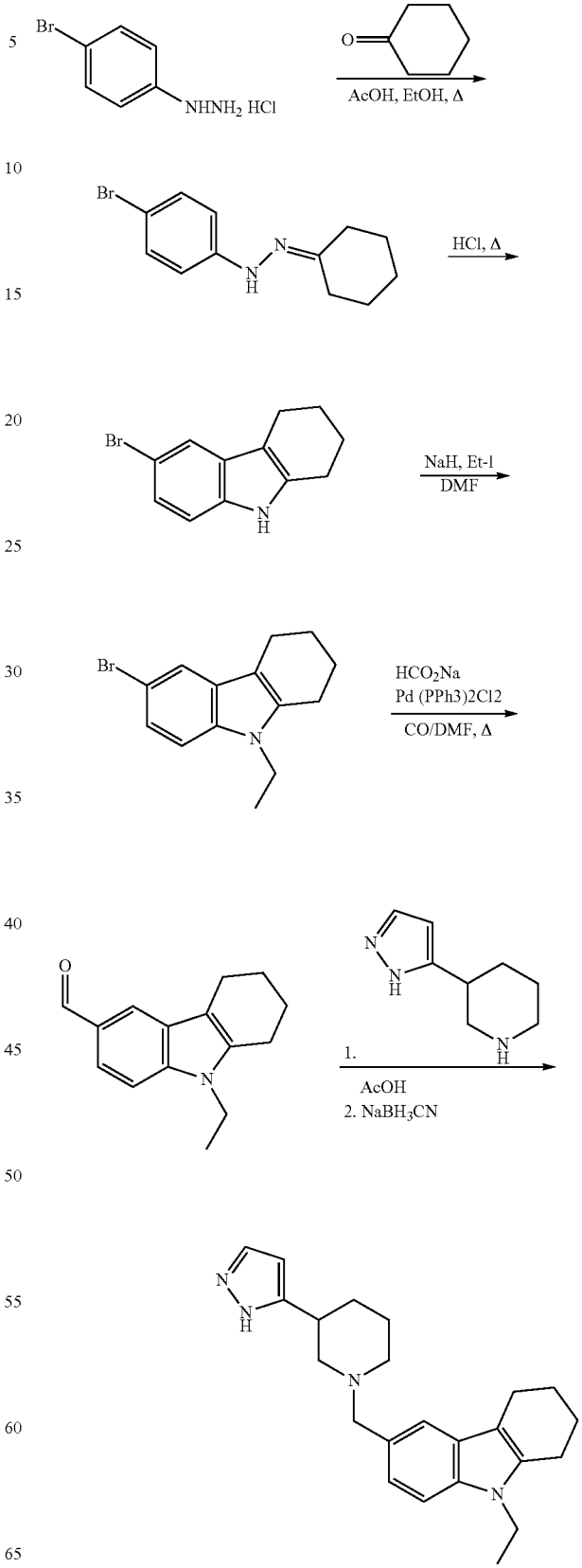

EXAMPLE 22

6-((3-(1H-pyrazol-5-yl)piperidin-1-yl)methyl)-9-ethyl-2,3,4,9-tetrahydro-1H-carbazole

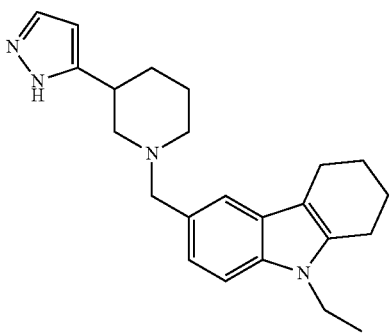

Step 1.
1-(4-Bromophenyl)-2-cyclohexylidenehydrazine

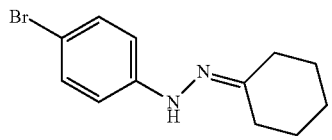

A 250-mL round-bottomed flask was charged with 1-(4-bromophenyl)hydrazine hydrochloride (10 g, 45.05 mmol, 1.00 equiv) in EtOH (120 mL). To this was added cyclohexanone (8.8 g, 89.80 mmol, 2.00 equiv) and acetic acid (2.7 g, 45.00 mmol, 1.00 equiv). The resulting mixture was heated to 105° C. in an oil bath for about 1 hour. The reaction progress was monitored by TLC (EtOAc:PE=1:1). Upon completion, the reaction mixture was cooled down to room temperature and filtered off to obtain 1-(4-bromophenyl)-2-cyclohexylidenehydrazine as a yellow solid (11 g, 92%).

Step 2. 6-Bromo-2,3,4,9-tetrahydro-1H-carbazole

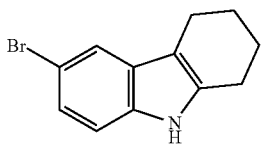

A 250-mL round-bottomed flask was charged with 1-(4-bromophenyl)-2-cyclohexylidenehydrazine (11 g, 41.35 mmol, 1.00 equiv) and conc. HCl (150 mL). The resulting mixture was heated to 60° C. in an oil bath for 4 hours. The reaction progress was monitored by TLC (EtOAc:PE=1:1). Upon completion, the reaction mixture was cooled down to room temperature. The pH was adjusted to 8 with aqueous sodium hydroxide. The resulting mixture was then extracted with ethyl acetate (5×100 mL). The combined organic layers were dried over anhydrous sodium sulfate, filtered off and concentrated on a rotary evaporator. The residue was purified by a silica gel column chromatography eluted with ethyl acetate/petroleum ether (1/10) affording 3-bromo-6,7,8,9-tetrahydro-5H-carbazole as yellow solid (10 g, 97%).

Step 3.
6-Bromo-9-ethyl-2,3,4,9-tetrahydro-1H-carbazole

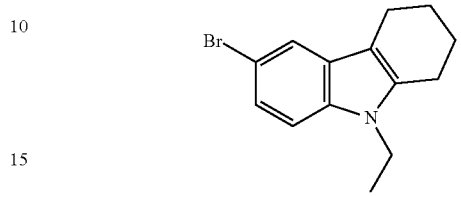

A 500-mL round-bottomed flask was charged with 3-bromo-6,7,8,9-tetrahydro-5H-carbazole (5 g, 20.08 mmol, 1.00 equiv) in N,N-dimethylformamide (270 mL). To this solution was added sodium hydride (1.2 g, 30.00 mmol, 1.50 equiv, 60%) in several batches at −10° C., followed by addition of iodoethane (6.26 g, 40.13 mmol, 2.00 equiv) as a solution in N,N-dimethylformamide (30 mL) drop wise −10° C. The resulting mixture was stirred at room temperature for 30 minutes. The reaction progress was monitored by TLC (EtOAc:PE=1:1). Upon completion, the reaction was then quenched by the addition of water/ice (120 mL). Then, the mixture was extracted with ethyl acetate (4×80 mL). The combined organic layers were dried over anhydrous sodium sulfate, filtered off and concentrated on a rotary evaporator. The residue was purified by a silica gel column chromatography eluted with ethyl acetate/petroleum ether (1/20) affording 3-bromo-9-ethyl-6,7,8,9-tetrahydro-5H-carbazole as brown oil (5 g, 90%).

Step 4. 9-Ethyl-2,3,4,9-tetrahydro-1H-carbazole-6-carbaldehyde

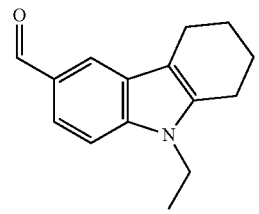

A 250-mL round-bottomed flask was charged with a solution of 3-bromo-9-ethyl-6,7,8,9-tetrahydro-5H-carbazole (2 g, 7.22 mmol, 1.00 equiv) in N,N-dimethylformamide (100 mL), sodium formate (740 mg, 10.88 mmol, 1.50 equiv), $Pd(PPh_3)_2Cl_2$ (500 mg, 0.72 mmol, 0.10 equiv) and CO (500 mL). The resulting solution was heated to 110° C. in an oil bath for 3 hours. The reaction progress was monitored by TLC (EtOAc:PE=1:5). Upon completion, the resulting solution was diluted with ethyl acetate (200 mL) and then quenched by the addition of brine (200 mL). The resulting mixture was extracted with ethyl acetate (2×100 mL) and the combined organic layers were dried over anhydrous sodium sulfate, filtered off and concentrated on a rotary evaporator affording 9-ethyl-6,7,8,9-tetrahydro-5H-carbazole-3-carbaldehyde as pale yellow solid (1.5 g, 70%).

Step 5. 6-((3-(1H-Pyrazol-5-yl)piperidin-1-yl)methyl)-9-ethyl-2,3,4,9-tetrahydro-1H-carbazole

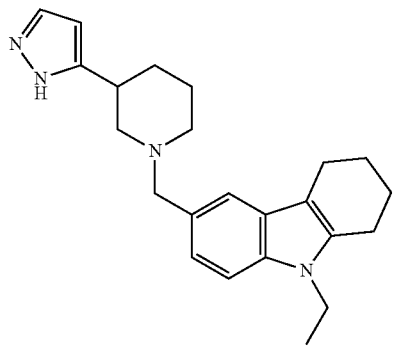

A 250-mL round-bottomed flask was charged a solution of 3-(1H-pyrazol-5-yl)piperidine dihydrochloride (2.9 g, 13.00 mmol, 1.50 equiv) in ethanol (150 mL) and DIPEA (4.55 g, 35.23 mmol, 4.00 equiv), acetic acid (3.17 g, 52.83 mmol, 6.00 equiv), 9-ethyl-6,7,8,9-tetrahydro-5H-carbazole-3-carbaldehyde (2 g, 8.81 mmol, 1.00 equiv) and NaBH$_3$CN (1.665 g, 26.43 mmol, 3.00 equiv). The resulting mixture was heated to 40° C. in an oil bath for 16 hours. The reaction progress was monitored by TLC (DCM: MeOH=10:1). Upon completion, the mixture was diluted with dichloromethane (200 mL). The pH was adjusted to 9 with aqueous sodium bicarbonate. The mixture was then extracted with dichloromethane (3×100 mL). Combined organic layers were dried over anhydrous sodium sulfate, filtered off and concentrated on a rotary evaporator. The residue was purified by a silica gel column chromatography eluted with dichloromethane/methanol (10/1) affording 3-((3-(1H-pyrazol-5-yl)piperidin-1-yl)methyl)-9-ethyl-6,7,8,9-tetrahydro-5H-carbazole as white solid (1 g, 30%). LCMS: [M+H]$^+$: 363. $^1$H NMR (CDCl$_3$, 300 MHz) δ 7.45 (d, 1H), 7.43 (s, 1H), 7.26 (d, 1H), 7.19 (d, 1H), 6.06 (d, 1H), 4.05 (m, 2H), 3.92 (m, 2H), 3.36 (br, 1H), 2.73 (m, 4H), 2.65 (br, 2H), 2.11 (s, 2H), 1.86 (m, 5H), 1.75 (br, 1H), 1.55 (m, 1H), 1.47 (m, 1H), 1.31 (t, 3H).

EXAMPLE 23

3-((3-(1H-1,2,3-triazol-5-yl)piperidin-1-yl)methyl)-9-ethyl-9H-carbazole

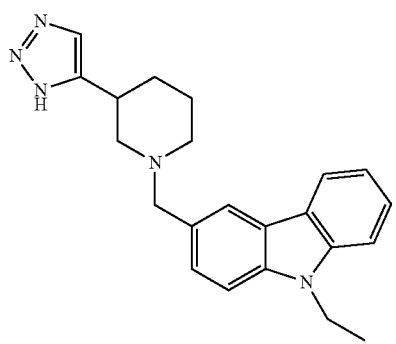

A 100-mL round-bottomed flask was charged with a solution of 3-(3H-1,2,3-triazol-4-yl)piperidine hydrochloride (500 mg, 3.29 mmol, 1.00 equiv) in ethanol (50 mL), 9-ethyl-9H-carbazole-3-carbaldehyde (890 mg, 3.99 mmol, 1.50 equiv), N-ethyl-N-isopropylpropan-2-amine (1.37 g, 10.62 mmol, 4.00 equiv), acetic acid (640 mg, 10.67 mmol, 4.00 equiv) and NaBH$_3$CN (510 mg, 8.10 mmol, 3.00 equiv). The resulting solution was heated to 40° C. in an oil bath for 16 hours. The reaction progress was monitored by TLC (DCM: MeOH=10:1). Upon completion, pH was adjusted to 8 with sodium bicarbonate/water. The resulting mixture was then extracted with dichloromethane (4×80 mL). Combined organic layers were dried over anhydrous sodium sulfate, filtered off and concentrated on a rotary evaporator. The residue was purified by a silica gel column chromatography eluted with dichloromethane/methanol (40/1) affording 3-((3-(3H-1,2,3-triazol-4-yl)piperidin-1-yl)methyl)-9-ethyl-9H-carbazole as white solid (0.5 g, 42%). LCMS: [M+H]$^+$: 360. $^1$H NMR (CDCl$_3$, 300 MHz) δ 8.08 (d, 1H), 8.03 (s, 1H), 7.47 (m, 3H), 7.26 (m, 2H), 4.35 (d, 2H), 3.80 (m, 2H), 3.30 (s, 1H), 2.99 (s, 2H), 2.80 (s, 1H), 2.61 (s, 2H), 1.94 (s, 1H), 1.73 (s, 2H), 1.54 (s, 1H), 1.42 (t, 3H).

EXAMPLE 24

3-((3-(1H-pyrazol-4-yl)piperidin-1-yl)methyl)-9-ethyl-9H-carbazole

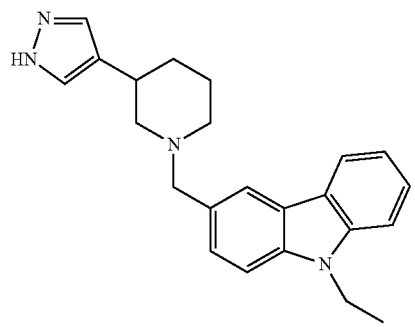

Step 1. 1-Benzyl-4-iodo-1H-pyrazole

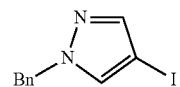

A 250-mL round-bottomed flask was charged with 4-iodo-1H-pyrazole (17 g, 87.63 mmol, 1.00 equiv) in N,N-dimethylformamide (150 mL) To this was added sodium hydride (3.6 g, 105.00 mmol, 1.20 equiv, 70%) in several batches at 0° C., followed by addition of 1-(bromomethyl)benzene (16.5 g, 96.49 mmol, 1.10 equiv) dropwise at 0° C. The resulting solution was allowed to warm up to room temperature and stirred for 2 hours at room temperature. The reaction was then quenched by the addition of water/ice (200 mL). The resulting solution was extracted with ethyl acetate (3×200 mL). Combined organic layers were dried over anhydrous sodium sulfate, filtered off and concentrated on a rotary evaporator affording 1-benzyl-4-iodo-1H-pyrazole as yellow solid (22 g, 80%).

Step 2. 1-Benzyl-4-(4,4,5,5-tetramethyl-1,3,2-dioxaborolan-2-yl)-1H-pyrazole

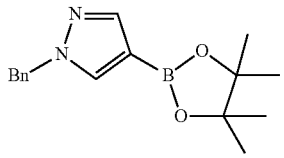

A 1000-mL 3-necked round-bottomed flask was charged with a solution of 1-benzyl-4-iodo-1H-pyrazole (32 g, 112.68 mmol, 1.00 equiv) in N,N-dimethylformamide (500 mL), 4,4,5,5-tetramethyl-2-(4,4,5,5-tetramethyl-1,3,2-dioxaborolan-2-yl)-1,3,2-dioxaborolane (31.5 g, 124.02 mmol, 1.10 equiv), Pd(dppf)Cl$_2$·CHCl$_3$ (2.8 g, 3.33 mmol, 0.03 equiv), AcOK (33.1 g, 337.76 mmol, 3.00 equiv). The resulting solution was heated to 85° C. in an oil bath overnight. The resulting mixture was diluted with water (200 mL). The solids were filtered out. The mixture was then extracted with ethyl acetate (3×200 mL). Combined organic layers were washed with brine (3×200 mL), dried over anhydrous sodium sulfate, filtered off and concentrated on a rotary evaporator. The residue was purified by a silica gel column chromatography eluted with ethyl acetate/petroleum ether (1:7) affording 1-benzyl-4-(4,4,5,5-tetramethyl-1,3,2-dioxaborolan-2-yl)-1H-pyrazole as white solid (20 g, 62%).

Step 3. Tert-butyl 3-(1-benzyl-1H-pyrazol-5-yl)-5,6-dihydropyridine-1(2H)-carboxylate

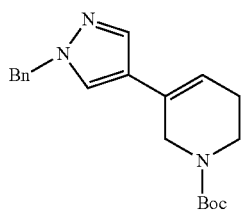

A 250-mL 3-necked round-bottomed flask was charged with a solution of tert-butyl 3-(trifluoromethylsulfonyloxy)-5,6-dihydropyridine-1(2H)-carboxylate (5.0 g, 15.11 mmol, 1.00 equiv) in toluene (100 mL), a solution of 1-benzyl-4-(4,4,5,5-tetramethyl-1,3,2-dioxaborolan-2-yl)-1H-pyrazole (4.29 g, 15.11 mmol, 1.00 equiv) in ethanol (100 mL), triethylamine (4.58 g, 45.35 mmol, 3.00 equiv), Pd(PPh$_3$)$_4$ (345 mg, 0.30 mmol, 0.01 equiv) and water (30 mL). The resulting mixture was heated to reflux for 3 hours. Upon completion, the mixture was diluted with water (100 mL). Then, it was extracted with ethyl acetate (3×200 mL). Combined organic layers were dried over anhydrous sodium sulfate and concentrated on a rotary evaporator. The residue was purified by silica gel column chromatography eluted with ethyl acetate/petroleum ether (1:5) affording tert-butyl 3-(1-benzyl-1H-pyrazol-4-yl)-5,6-dihydropyridine-1(2H)-carboxylate as yellow oil (5.0 g, 98%).

Step 4. Tert-butyl 3-(1H-pyrazol-4-yl)piperidine-1-carboxylate

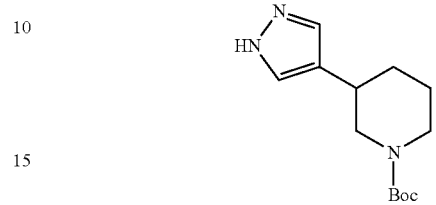

A 50-mL round-bottomed flask was charged with a solution of tert-butyl 3-(2-benzyl-2H-pyrrol-3-yl)-5,6-dihydropyridine-1(2H)-carboxylate (100 mg, 0.30 mmol, 1.00 equiv) in ethanol (20 mL), HCOOH (2 mL), and palladium on carbon (0.2 g). The resulting mixture was stirred for 2 hours at room temperature. Upon completion, the mixture was filtered through Celite and concentrated on a rotary evaporator affording tert-butyl 3-(1H-pyrazol-5-yl)piperidine-1-carboxylate as yellow oil (0.05 g, 67%).

Step 5. 3-(1H-Pyrazol-4-yl)piperidine hydrochloride

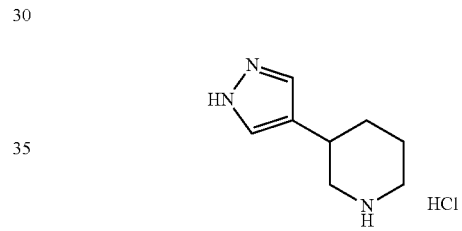

A 100-mL round-bottomed flask was charged with a solution of tert-butyl 3-(1H-pyrazol-4-yl)piperidine-1-carboxylate (3.6 g, 14.34 mmol, 1.00 equiv) in 1,4-dioxane (20 mL) and hydrogen chloride (6M, 20 mL). The resulting solution was heated to reflux for 1 hour. Upon completion, the resulting mixture was cooled down and concentrated on a rotary evaporator affording 3-(1H-pyrazol-4-yl)piperidine hydrochloride as white solid (1.5 g, 47%).

Step 6. 3-((3-(1H-Pyrazol-4-yl)piperidin-1-yl)methyl)-9-ethyl-9H-carbazole

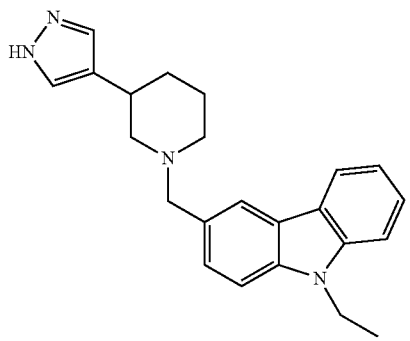

3-((3-(1H-Pyrazol-4-yl)piperidin-1-yl)methyl)-9-ethyl-9H-carbazole was prepared as described in Example 1. 3-(1H-Pyrazol-4-yl)piperidine hydrochloride was replaced for 3-(1H-pyrazol-5-yl)piperidine in Step 7 of Example 1. LCMS: [M+H]$^+$: 359. $^1$H NMR (DMSO-$d_6$, 300 MHz) δ 8.11-8.07 (m, 2H), 7.52-7.43 (m, 5H), 7.22-7.20 (m, 1H), 4.48-4.41 (m, 2H), 3.76-3.70 (m, 2H), 3.37-3.32 (m, 1H), 3.14-3.00 (m, 1H), 2.91-2.83 (m, 1H), 2.72 (s, 1H), 2.16-1.91 (m, 3H), 1.77-1.71 (m, 2H), 1.40 (s, 3H), 0.89-0.92 (s, 2H).

EXAMPLE 25

9-ethyl-3-((4-methylpiperazin-1-yl)methyl)-9H-carbazole

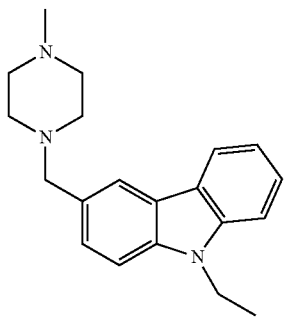

9-ethyl-3-((4-methylpiperazin-1-yl)methyl)-9H-carbazole was prepared as described in Example 1. 1-Methylpiperazine was replaced for 3-(1H-pyrazol-5-yl)piperidine in Step 7 of Example 1. LCMS: [M+H]$^+$: 308.

EXAMPLE 26

3-(3-((3-(1H-pyrazol-5-yl)piperidin-1-yl)methyl)-9H-carbazol-9-yl)-N,N-dimethylpropan-1-amine

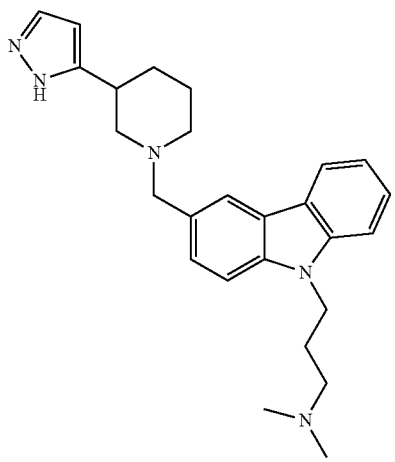

Step 1. 9-(3-Bromopropyl)-9H-carbazole

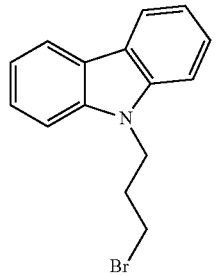

A 250-mL round-bottomed flask was charged with a solution of 9H-carbazole (5 g, 29.94 mmol, 1.00 equiv) in THF (200 mL). To this was added NaH (1.8 g, 75.00 mmol, 1.50 equiv) in small portions at and allowed to stir for 30 minutes. To the mixture was added 1,3-dibromopropane (18 g, 89.55 mmol, 3.00 equiv) at −10° C. and warmed up to 30° C. in an oil bath for 30 minutes. The reaction progress was monitored by TLC (EtOAc:PE=1:5). Upon completion, the reaction was then quenched by the addition of water (100 mL). The resulting mixture was extracted with ethyl acetate (3×50 mL). Combined organic layers were washed with brine (3×50 mL), dried over anhydrous sodium sulfate. Solids were filtered off and the mixture was concentrated on a rotary evaporator affording 9-(3-bromopropyl)-9H-carbazole as yellow solid (10 g).

Step 2.
3-(9H-carbazol-9-yl)-N,N-dimethylpropan-1-amine

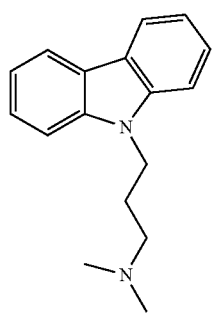

A 250-mL round-bottomed flask was charged with NaH (5.6 g, 140.00 mmol, 4.00 equiv, 60%) in DMF (100 mL). To this was added dimethylamine hydrochloride (4.23 g, 52.22 mmol, 1.50 equiv) in DMF (50 mL) at room temperature. To this mixture 9-(3-bromopropyl)-9H-carbazole (10 g, 34.70 mmol, 1.00 equiv) was added and the resulting mixture was stirred at room temperature for 4 hours. The reaction progress was monitored by TLC (DCM:MeOH=10:1). Upon completion, the reaction was then quenched by the addition of ice/salt (100 mL). The resulting mixture was extracted with ethyl acetate (3×50 mL). Combined organic layers were dried over anhydrous sodium sulfate, filtered and concentrated on a rotary evaporator affording 3-(9H-carbazol-9-yl)-N,N-dimethylpropan-1-amine as yellow oil (7.37 g, 80%).

Step 3. 9-(3-(Dimethylamino)propyl)-9H-carbazole-3-carbaldehyde

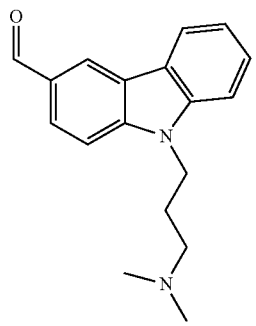

A 100-mL round-bottomed flask was charged with a solution of 3-(9H-carbazol-9-yl)-N,N-dimethylpropan-1-amine (500 mg, 1.98 mmol, 1.00 equiv) in DCM (10 mL), aluminum (III) chloride (550 mg, 4.17 mmol, 2.00 equiv), dichloro(methoxy)methane (0.24 mL, 1.10 equiv), water (10 mL) and $K_2CO_3$ (20 mL). The resulting mixture was stirred at 0° C. for 20 hours. The reaction progress was monitored by TLC (DCM: MeOH=10:1). Upon completion, the resulting solution was extracted with ethyl acetate (3×30 mL). Combined organic layers were dried over anhydrous sodium sulfate and concentrated on a rotary evaporator affording 9-(3-(dimethylamino)propyl)-9H-carbazole-3-carbaldehyde as yellow oil (0.45 g, 81%).

Step 4. 3-(3-((3-(1H-pyrazol-5-yl)piperidin-1-yl)methyl)-9H-carbazol-9-yl)-N,N-dimethyl propan-1-amine

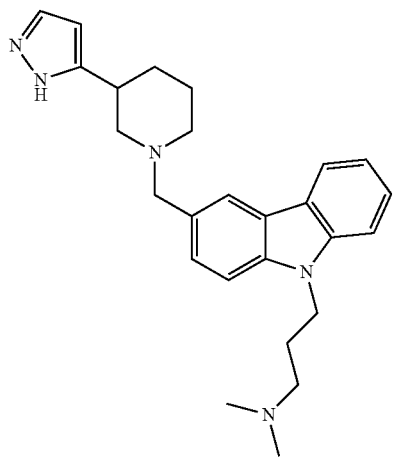

3-(3-((3-(1H-pyrazol-5-yl)piperidin-1-yl)methyl)-9H-carbazol-9-yl)-N,N-dimethyl propan-1-amine was prepared as described in Example 1. 9-(3-(dimethylamino)propyl)-9H-carbazole-3-carbaldehyde was replaced for 9-ethyl-9H-carbazole-3-carbaldehyde in Step 7 of Example 1. LCMS: [M+H]⁺: 416. ¹H NMR (CDCl₃, 300 MHz) δ 8.07 (d, 1H), 8.00 (s, 1H), 7.41 (m, 5H), 7.20 (m 1H), 6.03 (s, 1H), 4.37 (t, 2H), 3.72, 3.15 (s, 1H), 2.80-2.40 (br, 4H), 2.30 (s, 2H), 2.23 (s, 3H), 2.22 (s, 3H), 2.00 (t, 2H), 1.80 (m, 1H), 1.63 (t, 3H).

EXAMPLE 27

1-((9-(3-(dimethylamino)propyl)-9H-carbazol-3-yl)methyl)piperidine-3-carboxamide

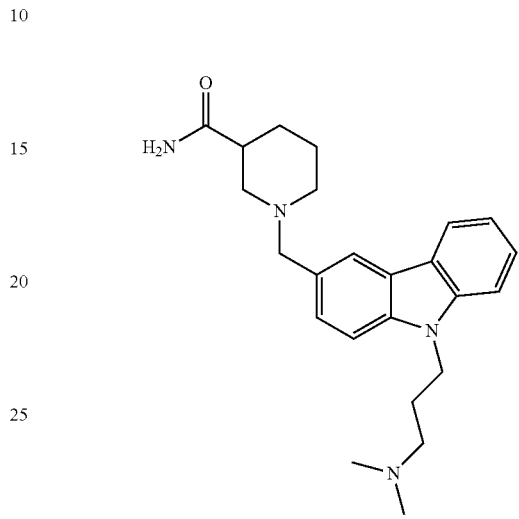

1-((9-(3-(dimethylamino)propyl)-9H-carbazol-3-yl)methyl)piperidine-3-carboxamide was prepared as described in Example 26. Piperidine-3-carboxamide was replaced for 3-(1H-pyrazol-5-yl)piperidine in Step 4 of Example 26. LCMS: [M+H]⁺: 393. ¹H NMR (CDCl₃, 300 MHz) δ 8.06 (d, 1H), 7.96 (s, 1H), 7.60-7.52 (m, 2H), 7.47-7.38 (m, 2H), 7.30 (m, 1H), 7.20 (m, 1H), 6.75 (s, 1H), 4.40 (m, 2H), 3.62 (m, 2H), 3.60 (br, 1H), 2.81 (m, 2H), 2.27-2.22 (m, 3H), 2.16 (s, 6H), 2.02-1.88 (m, 4H), 1.61-1.58 (m, 1H), 1.50-1.20 (m, 2H).

EXAMPLE 28

1-((9-(3-(dimethylamino)propyl)-9H-carbazol-3-yl)methyl)piperidin-3-amine

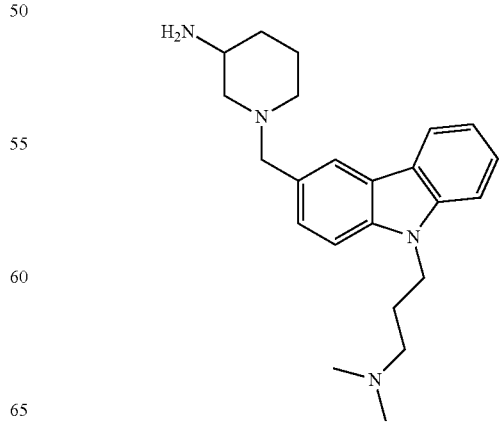

Step 1. tert-butyl 1-((9-(3-(dimethylamino)propyl)-9H-carbazol-3-yl)methyl)piperidin-3-yl carbamate

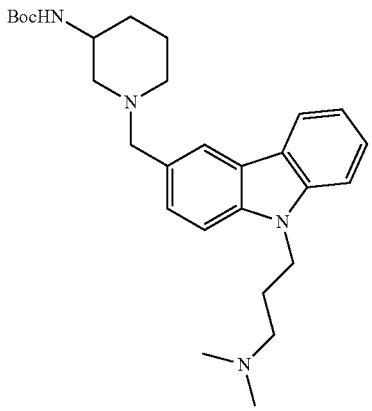

A 250-mL round-bottomed flask was charged with a solution of 9-(3-(dimethylamino)propyl)-9H-carbazole-3-carbaldehyde (800 mg, 2.86 mmol, 1.00 equiv) in EtOH (120 mL), tert-butyl piperidin-3-ylcarbamate (1.07 g, 5.35 mmol, 1.50 equiv), acetic acid (1.03 g, 17.17 mmol, 6.00 equiv) and NaBH$_3$CN (720 mg, 11.43 mmol, 4.00 equiv). The resulting mixture was stirred at 40° C. in an oil bath for 16 hours. The reaction progress was monitored by TLC (DCM: MeOH=10: 1). The reaction was then quenched by the addition of NaHCO$_3$ (50 mL). The mixture was then extracted with dichloromethane (4×50 mL). Combined organic layers were dried over anhydrous sodium sulfate, filtered off and concentrated on a rotary evaporator. The residue was purified by a silica gel column chromatography eluted with dichloromethane/methanol (50/1) affording tert-butyl 14(943-(dimethylamino)propyl)-9H-carbazol-3-yl)methyl)piperidin-3-yl carbamate as brown oil (0.5 g).

Step 2. 1-((9-(3-(dimethylamino)propyl)-9H-carbazol-3-yl)methyl)piperidin-3-amine dihydro chloride

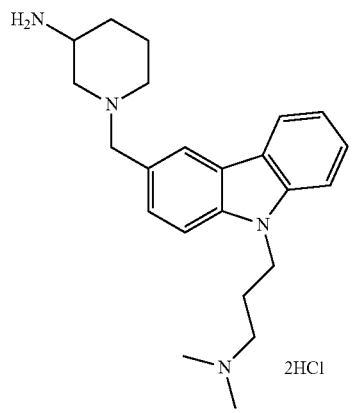

A 50-mL round-bottom flask was charged with tert-butyl 1-((9-(3-(dimethylamino)propyl)-9H-carbazol-3-yl)methyl)piperidin-3-ylcarbamate (200 mg, 0.43 mmol, 1.00 equiv) and conc. HCl (1 mL) in 1,4-dioxane (3 mL). The resulting mixture was stirred at room temperature for 1 hour. Upon completion, the resulting mixture was concentrated on a rotary evaporator to give the crude that was re-crystallized from 1:1 CH$_3$OH/ether affording 1-((9-(3-(dimethylamino)propyl)-9H-carbazol-3-yl)methyl)piperidin-3-amine dihydrochloride yellow solid (0.2 g, 98%). LCMS: [M+H]$^+$: 365. $^1$H NMR (D$_2$O, 300 MHz) δ 8.08-8.05 (m, 2H), 7.53-7.44 (m, 4H), 7.28-7.23 (m, 1H), 4.47 (br, 2H), 4.31 (t, 2H), 3.73 (br, 1H), 3.55-3.47 (m, 2H), 3.06-2.90 (m, 4H), 2.64 (s, 6H), 2.22-2.13 (m, 3H), 2.05-2.00 (m, 1H), 1.67-1.54 (m, 2H).

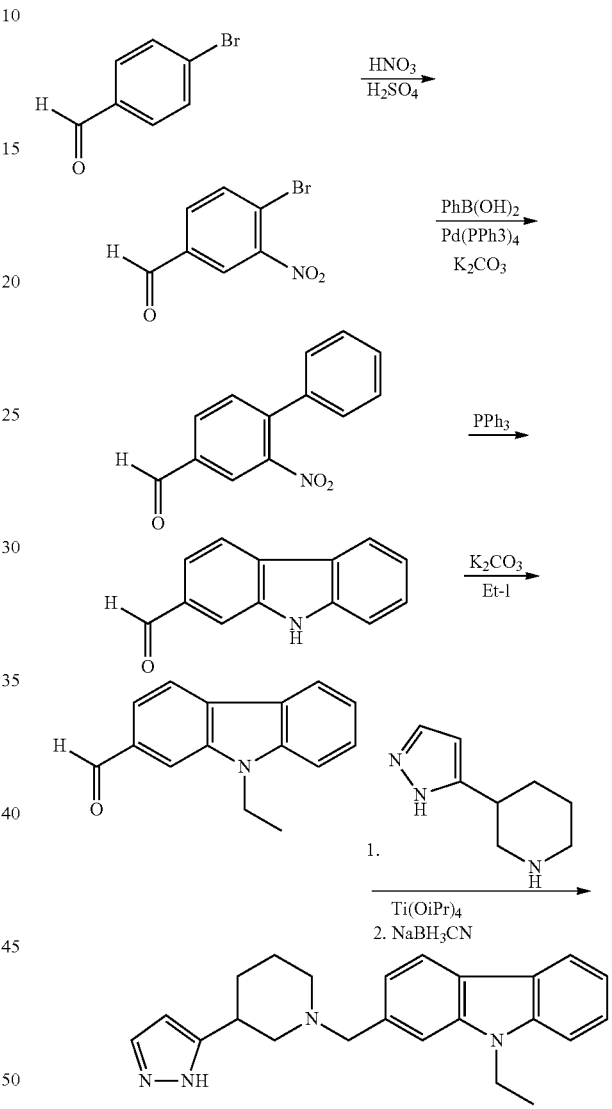

EXAMPLE 29

2-((3-(1H-pyrazol-5-yl)piperidin-1-yl)methyl)-9-ethyl-9H-carbazole

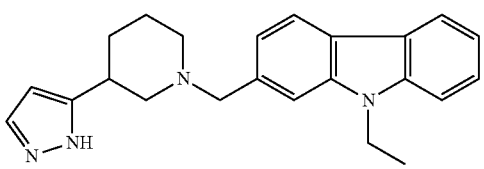

Step 1. 4-Bromo-3-nitrobenzaldehyde

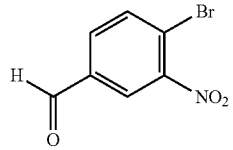

A 100-mL 3-necked round-bottom flask was charged with NaNO$_3$ (5.48 g, 64.47 mmol, 1.19 equiv). To this was added H$_2$SO$_4$ (60 mL, 98%). The resulting solution was stirred for 1.5 hours at 10° C. To the mixture was added 4-bromobenzaldehyde (10 g, 54.05 mmol, 1.00 equiv). The resulting solution was stirred for an additional 2 hours at 10° C. The reaction progress was monitored by TLC (EtOAc: PE=1:5). Upon completion, the reaction was then quenched by the addition of 200 g of ice. The solids were collected by filtration and washed with water (3×200 mL) affording 4-bromo-3-nitrobenzaldehyde as white solid (11.72 g, 94%).

Step 2. 2-Nitrobiphenyl-4-carbaldehyde

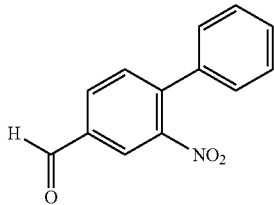

A 250-mL 3-necked round-bottom flask was charged with a solution of 4-bromo-3-nitrobenzaldehyde (11.5 g, 50.00 mmol, 1.00 equiv) in toluene (80 mL). To this was added phenylboronic acid (6.7 g, 54.92 mmol, 1.10 equiv), followed by the addition of a solution of K$_2$CO$_3$ (13.8 g, 100.00 mmol, 2.00 equiv) in water (50 mL). To the mixture was added Pd(PPh$_3$)$_4$ (1.2 g, 1.04 mmol, 0.02 equiv) in one portion. The resulting solution was stirred at 110° C. for 15 hours. Upon completion, the reaction mixture was cooled down to room temperature. The resulting solution was diluted with 1000 mL of Et$_2$O. The solids were filtered out. The resulting organic layers were washed with water (3×300 mL), dried over anhydrous magnesium sulfate and concentrated on a rotary evaporator. The residue was purified by silica gel column chromatography eluted with ethyl acetate/petroleum ether (1:50) to afford 2-nitrobiphenyl-4-carbaldehyde as yellow solid (6.7 g, 59%).

Step 3. 9H-Carbazole-2-carbaldehyde

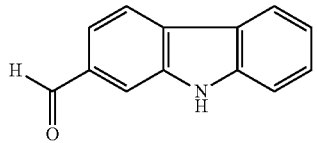

A 250-mL round-bottom flask was charged with 2-nitrobiphenyl-4-carbaldehyde (6.5 g, 28.63 mmol, 1.00 equiv), PPh$_3$ (18.8 g, 71.76 mmol, 2.50 equiv) and 1,2-dichlorobenzene (70 mL). The resulting solution was refluxed for 18 hours. The resulting mixture was concentrated under vacuum. The residue was purified by silica gel column chromatography eluted with ethyl acetate/petroleum ether (1:30) affording 9H-carbazole-2-carbaldehyde as yellow solid (3.7 g, 66%).

Step 4. 9-Ethyl-9H-carbazole-2-carbaldehyde

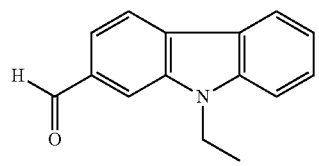

A 100-mL round-bottom flask was charged with a solution of 9H-carbazole-2-carbaldehyde (3.7 g, 18.97 mmol, 1.00 equiv) in DMF (50 mL). To this was added K$_2$CO$_3$ (5.23 g, 37.90 mmol, 2.00 equiv) followed by addition of bromoethane (10 g, 91.74 mmol, 4.80 equiv). The resulting solution was stirred overnight at room temperature. The reaction progress was monitored by TLC (EA:PE=1:3). Upon completion, the reaction mixture was quenched with water (100 mL). The resulting mixture was extracted with ethyl acetate (3×100 mL), combined organic layers were dried over sodium sulfate and concentrated on a rotary evaporator. The residue was purified by silica gel column chromatography eluted with ethyl acetate/petroleum ether (1:10) affording 9-ethyl-9H-carbazole-2-carbaldehyde as yellow solid (2.6 g, 61%).

Step 5. 2-((3-(1H-Pyrazol-5-yl)piperidin-1-yl)methyl)-9-ethyl-9H-carbazole

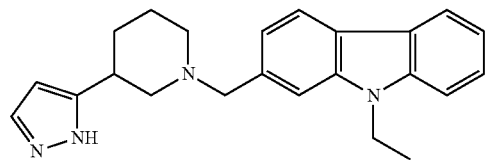

A 100-mL 3-necked round-bottom flask was charged with a solution of 9-ethyl-9H-carbazole-2-carbaldehyde (1.12 g, 5.02 mmol, 1.00 equiv) in THF (50 mL). To this was added 3-(1H-pyrazol-5-yl)piperidine hydrochloride (940 mg, 5.01 mmol, 1.00 equiv), Ti(O$^i$Pr)$_4$ (2 g, 7.04 mmol, 1.40 equiv) and TEA (660 mg, 6.52 mmol, 1.30 equiv). The resulting solution was stirred at room temperature overnight. To the mixture was then added NaBH$_3$CN (1.26 mg, 0.02 mmol, 4.00 equiv). The resulting solution was stirred at room temperature for 4 hours. Upon completion, the reaction was then quenched by the addition of water (50 mL). The resulting solution was extracted with ethyl acetate (4×50 mL) and the combined organic layers were dried over anhydrous magnesium sulfate and concentrated on a rotary evaporator. The residue was purified by silica gel column chromatography eluted with ethyl acetate/petroleum ether (1:10) affording 2-((3-(1H-pyrazol-5-yl)piperidin-1-yl)methyl)-9-ethyl-9H-carbazole as a white solid (0.3 g, 17%). LCMS:[M+H]$^+$ 359. $^1$H NMR (CDCl$_3$, 300 MHz) δ 8.08 (t, 2H), 7.50-7.41 (m, 4H), 7.28-7.21 (m, 2H), 6.05 (d, 1H), 4.40 (q, 2H), 3.80 (q, 2H), 3.16 (s, 1H), 2.72 (br, 4H), 1.88 (s, 1H), 1.65 (d, 3H), 1.46 (t, 3H).

SCHEME 5

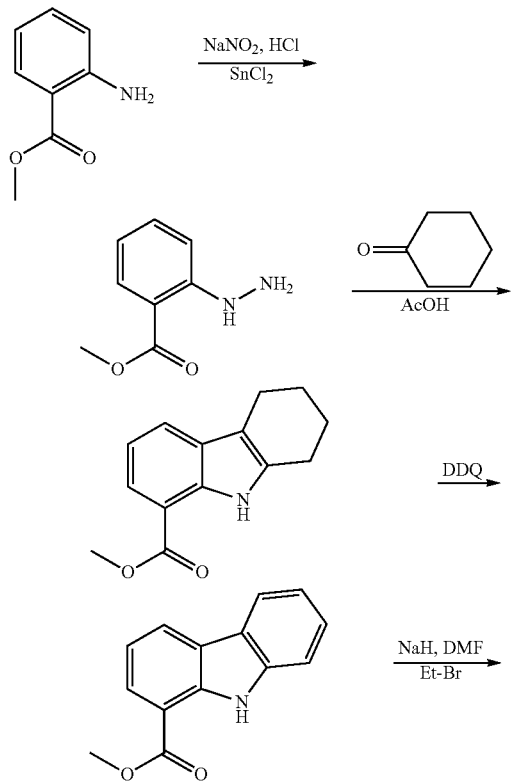

EXAMPLE 30

1-((3-(1H-pyrazol-5-yl)piperidin-1-yl)methyl)-9-ethyl-9H-carbazole

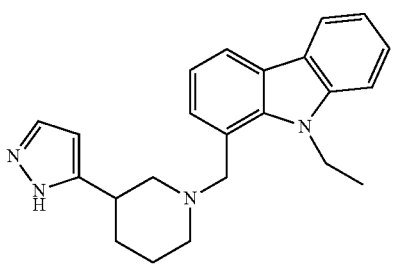

Step 1. Methyl 2-hydrazinylbenzoate

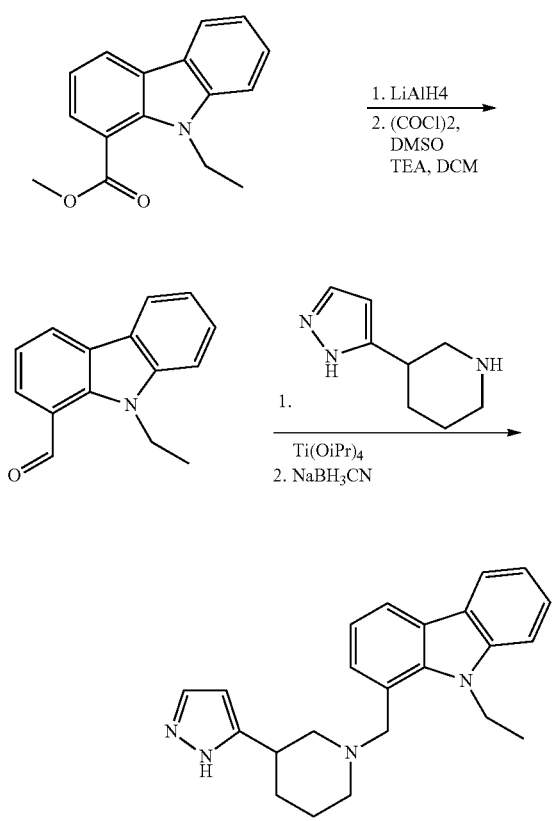

A 100-mL round-bottom flask was a solution of methyl 2-aminobenzoate (1 g, 6.62 mmol, 1.00 equiv) in HCl (30%, 10 mL). To this solution was added a solution of NaNO$_2$ (500 mg, 7.25 mmol, 1.02 equiv) in H$_2$O (10 mL) dropwise at 0° C. over 5 minutes. The resulting mixture was stirred at 0° C. for 30 minutes. Then, a solution of SnCl$_2$.2H$_2$O (2.75 g, 12.19 mmol, 2.00 equiv) in HCl (30%) (12 mL) was added dropwise at 0° C. The resulting solution was stirred for an additional 2 hours at room temperature. The solids were collected by filtration and washed with H$_2$O (2×20 mL) affording methyl 2-hydrazinylbenzoate as white solid (0.6 g, 55%).

Step 2. Methyl 2,3,4,9-tetrahydro-1H-carbazole-8-carboxylate

A 150-mL round-bottom flask was placed a solution of methyl 2-hydrazinylbenzoate (7.81 g, 1.00 equiv, 1%) in AcOH (70 mL). To this solution was added cyclohexanone (4.5 g, 45.92 mmol, 1.00 equiv) dropwise with stirring at 80° C. The resulting solution was heated to reflux for 2 hr in an oil bath. Upon completion, the reaction was then quenched with water (50 mL). The solids were collected by filtration and washed with H$_2$O (2×50 mL) affording methyl 6,7,8,9-tetrahydro-5H-carbazole-1-carboxylate as white solid (6 g, 55.8%).

Step 3. Methyl 9H-carbazole-1-carboxylate

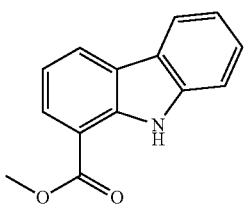

A 500-mL round-bottom flask was charged a solution of methyl 6,7,8,9-tetrahydro-5H-carbazole-1-carboxylate (13.5 g, 58.95 mmol, 1.00 equiv) in toluene (200 mL). To the mixture was added DDQ (15.98 g, 70.71 mmol, 1.20 equiv) in one portion. The resulting solution was heated to reflux for 2 hours in an oil bath. Upon completion, the resulting mixture was concentrated on a rotary evaporator. The residue was purified by a silica gel column chromatography eluted with dichloromethane/methanol (50:1) affording 9H-carbazole-1-carboxylate as white solid (10.5 g, 79%).

Step 4. Methyl 9-ethyl-9H-carbazole-1-carboxylate

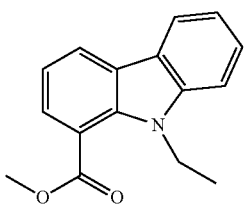

A 100-mL round-bottom flask was charged with a solution of methyl 9H-carbazole-1-carboxylate (2 g, 8.89 mmol, 1.00 equiv) in DMF (20 mL). To this was added NaH (1.78 g, 74.17 mmol, 5.00 equiv) in several batches followed by addition of bromoethane (1.92 g, 17.94 mmol, 2.00 equiv). The resulting solution was stirred at room temperature for 6 hours. Upon completion, the reaction was then quenched with water (20 mL). The mixture was then extracted with ethyl acetate (3×20 mL). Combined organic layers were dried over anhydrous sodium sulfate, filtered off and concentrated on a rotary evaporator. The residue was purified by a silica gel column chromatography eluted with dichloromethane/methanol (50:1) affording methyl 9-ethyl-9H-carbazole-1-carboxylate as light yellow solid (1.3 g, 58%).

Step 5. 9-Ethyl-9H-carbazole-1-carbaldehyde

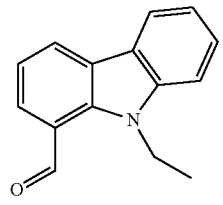

A 50-mL round-bottom flask was placed a solution of methyl 9-ethyl-9H-carbazole-1-carboxylate (1.3 g, 5.14 mmol, 1.00 equiv) in THF (50 mL). To the mixture was added LiAlH$_4$ (840 mg, 22.11 mmol, 4.00 equiv) in several batches at 0° C. and allowed to stir at this temperature 30 minutes. Then, the reaction was quenched with aqueous NaOH (2M, 12 mL). The mixture was then extracted with ethyl acetate (3×50 mL). Combined organic layers were dried over anhydrous sodium sulfate, filtered off and concentrated on a rotary evaporator. The residue was purified by a silica gel column chromatography eluted with dichloromethane/methanol (50:1) affording (9-ethyl-9H-carbazol-1-yl)methanol as white solid (1 g, (86%). Meanwhile, a 250-mL 3-necked round-bottom was charged with a solution of (COCl)$_2$ (840 mg, 6.67 mmol, 1.50 equiv) in DCM (40 mL). To this was added DMSO (1 g, 12.80 mmol, 3.00 equiv)-78° C. and allowed to stir for 30 min at this temperature. To this solution was added a solution of (9-ethyl-9H-carbazol-1-yl)methanol (1 g, 4.44 mmol, 1.00 equiv) in DCM (5 mL) at −78° C. The resulting solution was stirred at −78° C. for 5 hours. Then, triethylamine (TEA) (10 mL) was added and allowed to stir an additional hour at −78° C. Upon completion, the reaction was quenched with water and extracted with DCM (3×50 mL). Combined organic layers were dried over anhydrous sodium sulfate, filtered off and concentrated on a rotary evaporator. The residue was purified by a silica gel column chromatography eluted with dichloromethane/methanol (50:1) affording 9-ethyl-9H-carbazole-1-carbaldehyde as light yellow solid (0.9 g, 90.8%).

Step 6. 1-((3-(1H-Pyrazol-5-yl)piperidin-1-yl)methyl)-9-ethyl-9H-carbazole

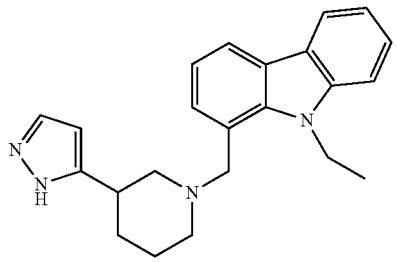

1-((3-(1H-Pyrazol-5-yl)piperidin-1-yl)methyl)-9-ethyl-9H-carbazole was prepared as described in Example 29. 9-Ethyl-9H-carbazole-1-carbaldehyde was replaced for 9-ethyl-9H-carbazole-2-carbaldehyde in Step 5 of Example 29. LCMS: [M+H]$^+$: 359. $^1$H NMR (CDCl$_3$, 300 MHz) δ 8.09 (t, 2H), 7.48 (m, 3H), 7.25 (m, 2H), 7.15 (t, 1H), 6.05 (s, 1H), 4.81 (q, 2H), 3.82 (s, 2H), 3.01 (s, 2H), 2.78 (s, 1H), 1.99 (m, 2H), 1.58 (m, 1H), 1.44 (m, 3H), 1.28 (t, 3H).

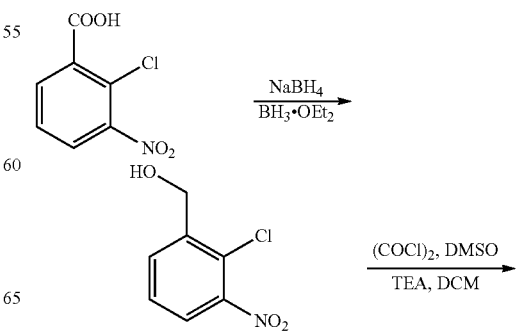

71

-continued

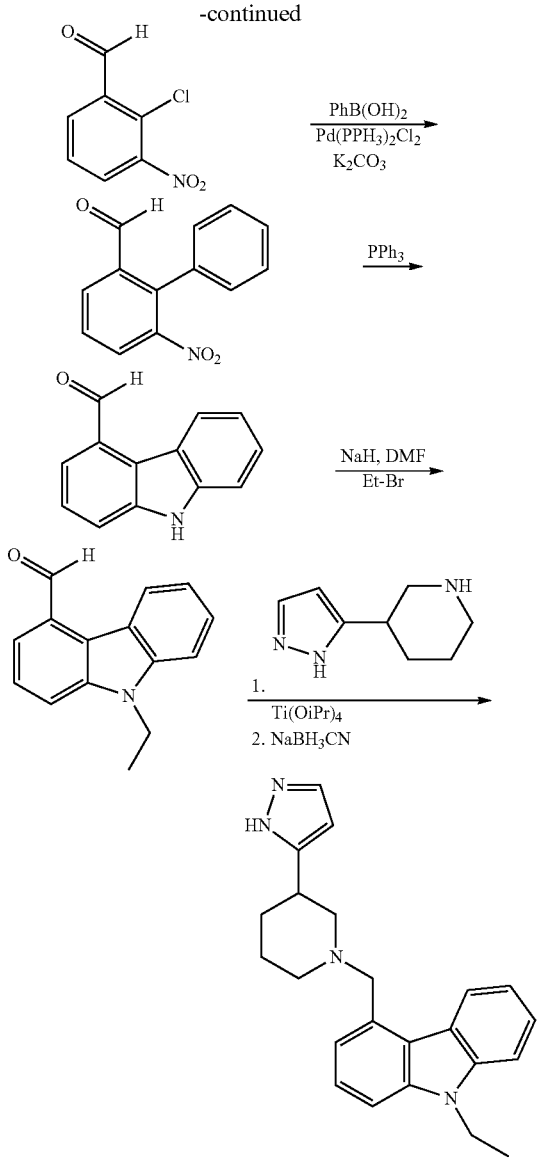

EXAMPLE 31

4-((3-(1H-pyrazol-5-yl)piperidin-1-yl)methyl)-9-ethyl-9H-carbazole

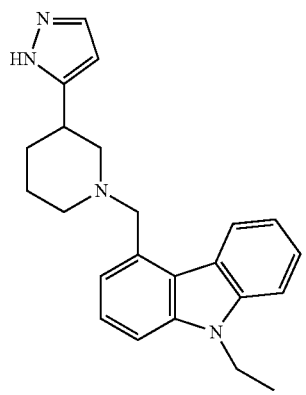

72

Step 1. (2-Chloro-3-nitrophenyl)methanol

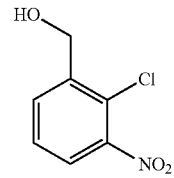

A 500-mL 3-necked round-bottom flask was charged with a solution of NaBH$_4$ (4 g, 105.26 mmol, 2.10 equiv) in THF (100 mL). To this was added a solution of 2-chloro-3-nitrobenzoic acid (10 g, 49.75 mmol) in THF (100 mL) at 0° C. After 10 minutes, BF$_3$.Et$_2$O (15 mL) in THF (50 mL) was added dropwise over 10 minutes. The resulting solution was stirred at room temperature overnight. The reaction progress was monitored by TLC (DCM: MeOH=5:1). Upon completion, the reaction was quenched with water (500 mL) and extracted with ethyl acetate (3×300 mL). Combined organic layers were dried over anhydrous sodium sulfate, filtered off and concentrated on a rotary evaporator affording (2-chloro-3-nitrophenyl)methanol as light yellow solid (9 g, 98%).

Step 2. 2-Chloro-3-nitrobenzaldehyde

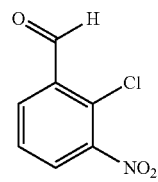

A 250-mL 3-necked round-bottom flask was charged with a solution of oxalyl chloride (5.42 g, 42.70 mmol, 1.10 equiv) in DCM (100 mL). To this was added a solution of DMSO (6.65 g, 85.11 mmol, 2.20 equiv) in DCM (15 mL) drop wise −78° C. 2-Chloro-3-nitrophenyl)methanol (7.23 g, 38.54 mmol, 1.00 equiv) in DCM (35 mL) was added into the solution at −78° C. and allowed to stir for 1 hour. Then, TEA (30 mL) was added at this temperature and allowed to stir for an additional hour. Upon completion, the reaction was quenched with water and extracted with DCM (3×100 mL). Combined organic layers were dried over anhydrous sodium sulfate, filtered off and concentrated on a rotary evaporator. The residue was purified by a silica gel column chromatography eluted with PE:EA (10:1) affording 2-chloro-3-nitrobenzaldehyde as light yellow solid (5.3 g, 74%).

Step 3. 6-Nitrobiphenyl-2-carbaldehyde

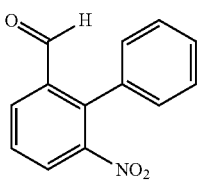

A 250-mL 3-necked round-bottom flask was placed a solution of 2-chloro-3-nitrobenzaldehyde (5.3 g, 28.57 mmol, 1.00 equiv) in toluene (50 mL), phenylboronic acid (3.83 g, 31.39 mmol, 1.10 equiv), K₂CO₃ (7.88 g, 57.10 mmol, 2.00 equiv) in water (30 mL) and Pd(PPh₃)₄ (660 mg, 0.57 mmol, 0.02 equiv). The resulting mixture was heated to 110° C. for 30 hours. Upon completion, the reaction mixture was cooled and diluted with Et₂O (1000 mL). After phase separation, organic layers were dried over anhydrous magnesium sulfate, filtered off and concentrated on rotary evaporator. The residue was purified by a silica gel column chromatography eluted with ethyl acetate/petroleum ether (1:50) affording 6-nitrobiphenyl-2-carbaldehyde as yellow solid (5.35 g, 82%).

Step 4. 9H-Carbazole-4-carbaldehyde

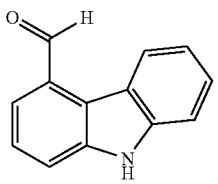

A 100-mL round-bottom flask was placed a solution of 6-nitrobiphenyl-2-carbaldehyde (6.2 g, 27.31 mmol, 1.00 equiv) in 1,2-dichlorobenzene (60 mL). To the mixture was added PPh₃ (17.9 g, 68.32 mmol, 2.50 equiv) and the mixture was heated to reflux for 30 hours. Upon completion, the resulting mixture was concentrated on a rotary evaporator to give a residue that was purified by silica gel column chromatography affording 9H-carbazole-4-carbaldehyde as yellow solid (3 g, 56%).

Step 5. 9-Ethyl-9H-carbazole-4-carbaldehyde

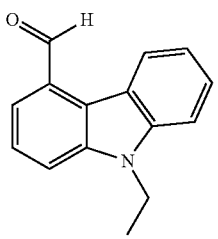

9-Ethyl-9H-carbazole-4-carbaldehyde was prepared as described in Step 4 of Example 30. After silica gel chromatography eluted with ethyl acetate/petroleum ether (1:30) afforded 9-ethyl-9H-carbazole-4-carbaldehyde as yellow solid (2.67 g, 78%).

Step 6. 4-((3-(1H-Pyrazol-5-yl)piperidin-1-yl)methyl)-9-ethyl-9H-carbazole

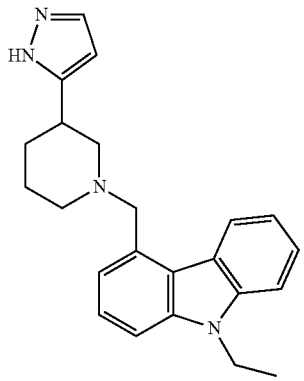

4-((3-(1H-Pyrazol-5-yl)piperidin-1-yl)methyl)-9-ethyl-9H-carbazole was prepared as described in Example 29. 9-Ethyl-9H-carbazole-4-carbaldehyde was replaced for 9-ethyl-9H-carbazole-2-carbaldehyde in Step 5 of Example 29. LCMS: [M+H]⁺: 359. ¹H NMR (CDCl₃, 300 MHz) δ 8.27 (d, 2H), 7.58-7.20 (m, 7H), 5.99 (s, 1H), 4.41 (q, 2H), 4.31 (d, 1H), 4.07 (d, 1H), 3.16 (s, 1H), 2.87-2.74 (br, 4H), 1.90 (d, 1H), 1.73-1.63 (m, 3H), 1.46 (t, 3H).

EXAMPLE 32

9-ethyl-4-((4-methylpiperazin-1-yl)methyl)-9H-carbazole

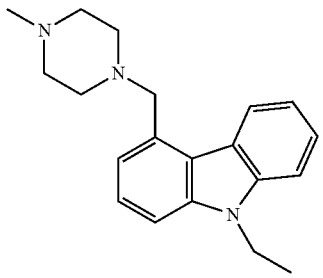

9-ethyl-4-((4-methylpiperazin-1-yl)methyl)-9H-carbazole was prepared as described in Example 31. 1-Methylpiperazine was replaced for 3-(1H-pyrazol-5-yl)piperidine in Step 6 of Example 31. LCMS: [M+H]⁺: 307. ¹H NMR (CDCl₃, 300 MHz) δ 8.36-8.33 (m, 1H), 7.55-7.23 (m, 6H), 4.44-4.37 (q, 2H), 4.12 (s, 2H), 2.72 (s, 4H), 2.51 (br, 4H), 2.28 (s, 3H), 1.47 (t, 3H).

EXAMPLE 33

9-ethyl-1-((4-methylpiperazin-1-yl)methyl)-9H-carbazole

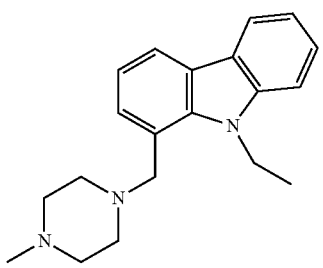

9-ethyl-1-((4-methylpiperazin-1-yl)methyl)-9H-carbazole was prepared as described in Example 30. 1-Methylpiperazine was replaced for 3-(1H-pyrazol-5-yl)piperidine in Step 6 of Example 30. LCMS: [M+H]$^+$: 308. $^1$H NMR (CDCl$_3$, 300 MHz) δ 8.11 (t, 2H), 7.47 (m, 2H), 7.27 (m, 2H), 7.16 (t, 1H), 4.81 (q, 2H), 3.88 (s, 2H), 2.46 (m, 8H), 2.32 (s, 3H), 1.50 (t, 3H).

EXAMPLE 34

9-ethyl-2-((4-methylpiperazin-1-yl)methyl)-9H-carbazole

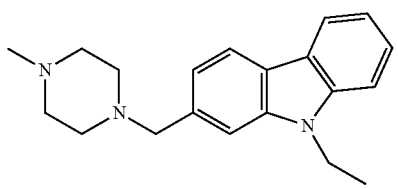

9-ethyl-2-((4-methylpiperazin-1-yl)methyl)-9H-carbazole was prepared as described in Example 29. 1-Methylpiperazine was replaced for 3-(1H-pyrazol-5-yl)piperidine in Step 5 of Example 29. LCMS: [M+H]$^+$: 308. $^1$H NMR (CDCl$_3$, 300 MHz) δ 8.11 (m, 2H), 7.34 (m, 3H), 7.23 (m, 1H), 7.15 (d, 1H), 4.38 (q, 2H), 3.85 (s, 2H), 2.86 (s, 4H), 2.71 (s, 4H), 2.67 (s, 3H), 1.35 (t, 3H).

The activity of the compounds in Examples 1-34 as H$_1$R and/or H$_4$R inhibitors is illustrated in the following assay. The other compounds listed above, which have not yet been made and/or tested, are predicted to have activity in these assay as well.

Biological Activity Assay

In Vitro Histamine Receptor Cell-Based Assays

The assays are based on an aequorin dependent bioluminescence signal, generated by receptor signaling through G$_{q/11}$ or a similarly acting G protein and a resulting transient calcium flux. Doubly-transfected, stable CHO-K1 cell lines expressing human histamine receptor type 1 or type 4, mitochondrion-targeted aequorin, and (histamine type 4 receptor only) human G protein Gα16 are obtained from Perkin-Elmer (Histamine H$_1$ cell line, catalog ES-390-A; Histamine H$_4$ cell line, catalog ES-393-A). Cells are maintained on conventional culture plasticware in F12 (Ham's) growth medium containing 10% (vol./vol.) fetal bovine serum, penicillin (100 IU/ml), streptomycin (0.1 mg/ml), zeocin (0.25 mg/ml) and geneticin (0.40 mg/ml), as per the manufacturer's instructions (all components from Invitrogen, Inc.). One day prior to assay, the growth medium is replaced with the same, excluding zeocin and geneticin.

To prepare cells for a histamine receptor assay, growth medium is aspirated, and the cells are rinsed with calcium-free, magnesium-free phosphate-buffered saline. The rinse is aspirated and replaced with Versene (Invitrogen, Inc.) and the cells incubated for two to three minutes at 37° C., followed by tapping the plate to fully dislodge cells. Assay medium (DMEM:F12 [50:50], phenol-red free, containing 1 mg/ml protease-free bovine serum albumin) is added to collect the cells, which are then transferred to a conical tube for centrifugation. The cell pellet is re-suspended in assay medium, and the cell density is determined by counting with a hemacytometer. The cells are then centrifuged again and re-suspended in assay medium to a final density of 5×10$^6$ cells/ml. Coelenterazine-h dye (500 μM in ethanol) is then added to a final concentration of 5 μM, and mixed immediately. The conical tube containing the cells is then wrapped with foil to protect the light sensitive dye. The cells are incubated for four hours further at normal room temperature (approximately 21° C.) with vertical rotation to keep them in suspension.

Just before assay, the dye-loaded cells are diluted to 0.75× 10$^6$ cells/ml (H$_1$ receptor) or 1.5×10$^6$ cells/ml (H$_4$ receptor) with additional assay medium. Cells are dispensed to 1536 well microtiter plates at 3 μl/well. To assay receptor antagonist activity, 60 mL of 100× concentration test compounds in dimethyl sulfoxide (DMSO) are dispensed to the wells, one compound per well, by passive pin transfer, and the plates are incubated for 15 minutes at room temperature. Assay plates are then transferred to a Lumilux (Perkin-Elmer) bioluminescence plate reader equipped with an automated 1536 well disposable tip pipette. The pipette then dispenses 3 μl/well of agonist (histamine, at twice the final concentration, where final concentration is a previously determined EC80 for response), with concurrent bioluminescence detection.

To assay receptor agonist activity, 60 mL of 100× concentration test compounds in DMSO are dispensed by passive pin transfer to 1536 well microtiter plates, one compound per well, that have previously received 3 μl/well of assay medium only. The plate is transferred to the Lumilux instrument, and 3 μl/well of cells (prepared as described above) are added by the 1536 well pipette from an onboard cell stirrer and reservoir apparatus, with concurrent bioluminescence detection.

CCD imaging capture on the Lumilux instrument includes a 5 second baseline read prior to agonist addition, generally with a 40 second complete read per plate. A decrease in bioluminescence signal (measured either as area-under-the-curve, or maximum signal amplitude minus minimum signal amplitude) correlates with receptor antagonism. Negative control activity is measured with DMSO lacking any test compound. For receptor antagonist assays, positive control activity is measured with diphenhydramine (2-Diphenyl-methoxy-N,N-dimethylethylamine, 10 μM final concentration, H$_1$ receptor) or JNJ7777120 (1-[(5-Chloro-1H-indol-2-yl)carbonyl]-4-methyl-piperazine, 10 μM final concentration, H$_4$ receptor). For receptor agonist assays, positive activity is measured with histamine (10 μM final concentration). Efficacy is measured as a percentage of positive control activity.

TABLE 1

| Biological Activity | | |
|---|---|---|
| Example | H$_1$R Antagonist Assay IC$_{50}$ | H$_4$R Antagonist Assay IC$_{50}$ |
| 1 | 0.54 | 1.07 |
| 2 | 11.1 | 2.23 |
| 3 | 3.12 | 3.06 |
| 4 | 18.2 | 9.62 |
| 5 | 5.94 | 8.09 |
| 6 | 5.97 | 4.39 |
| 7 | 5.57 | 3.83 |
| 8 | 7.55 | 8.5 |
| 9 | 46.4 | 12.6 |
| 10 | 0.68 | 0.18 |
| 11 | 9.91 | 6.15 |
| 12 | 3.16 | 1.46 |
| 13 | 2.56 | 1.03 |

TABLE 1-continued

Biological Activity

| Example | $H_1R$ Antagonist Assay $IC_{50}$ | $H_4R$ Antagonist Assay $IC_{50}$ |
| --- | --- | --- |
| 14 | 0.69 | 0.33 |
| 15 | 37.6 | 52.6 |
| 16 | 0.95 | 0.34 |
| 17 | 0.53 | 2.28 |
| 18 | 1.72 | 2.28 |
| 19 | 0.59 | 0.99 |
| 20 | 3.38 | 1.1 |
| 21 | 1.35 | 2.75 |
| 22 | 8.72 | 5.9 |
| 23 | 0.09 | 0.96 |
| 24 | 0.57 | 4.34 |
| 25 | 2.58 | 0.66 |
| 26 | 21.1 | 19.8 |
| 27 | >30 | >30 |
| 28 | >30 | 55.9 |
| 29 | 6.74 | 32.1 |
| 30 | >100 | 37.4 |
| 31 | 14.8 | 18.4 |
| 32 | >30 | 21.9 |
| 33 | 19 | 9.64 |
| 34 | 35.4 | 8.55 |

Compositions

The following are examples of compositions which may be used to topically deliver compounds disclosed herein, for example to the eye or nasal passages.

| Ingredients | Concentration (w/v %) |
| --- | --- |
| COMPOSITION EXAMPLE 1 | |
| Compound of Formula (I) | 0.01-2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |
| COMPOSITION EXAMPLE 2 | |
| Compound of Formula (I) | 0.01-2% |
| Hydroxypropyl guar | 0.4-6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |
| COMPOSITION EXAMPLE 3 | |
| Compound of Formula (I) | 0.01-2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of Formula III

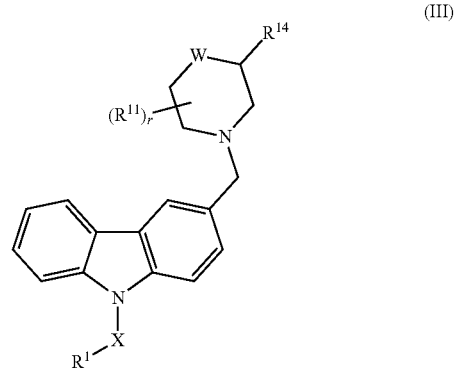

or a pharmaceutically acceptable salt, ester, or prodrug thereof, wherein

X is chosen from lower alkyl, lower alkenyl, and lower alkynyl, any of which may be optionally substituted with one or more substituents chosen from halogen, hydroxy, and cyano;

$R^1$ is chosen from hydrogen, hydroxy, lower cycloalkyl, lower heterocycloalkyl, lower amino, thio, carboxy, amido, and acyl;

W is chosen from C, N, and O;

r is 0-3;

each $R^{11}$ is individually chosen from hydrogen, halogen, hydroxy, lower hydroxyalkyl, lower alkyl, halogen, lower haloalkyl, lower alkoxy, lower haloalkoxy, monocyclic 5-membered heteroaryl, $C(O)OR^{12}$, $C(O)N(R^{12})(R^{13})$, perfluoromethyl, and perfluoromethoxy;

$R^{12}$ and $R^{13}$ are individually chosen from hydrogen, lower alkyl, lower cycloalkyl, lower cycloalkylalkyl, lower heterocycloalkyl, lower heterocycloalkylalkyl, lower heteroaryl, lower heteroarylalkyl, any of which may be optionally substituted with one or more substituents chosen from halogen, hydroxy, cyano, lower alkyl, lower alkenyl, lower alkynyl, lower heteroalkyl, lower alkoxy, lower haloalkyl, and lower haloalkoxy; and $R^{14}$ is an unsubstituted five-membered monocyclic heteroaryl.

2. The compound as recited in claim 1 wherein:

X is lower alkyl;

$R^1$ is hydrogen;

each $R^{11}$ is individually chosen from lower hydroxyalkyl, lower alkyl, monocyclic 5-membered heteroaryl, $C(O)OR^{12}$, and $C(O)N(R^{12})(R^{13})$; and $R^{12}$ and $R^{13}$ are chosen from hydrogen and lower alkyl.

3. The compound as recited in claim 1 of structural formula IV:

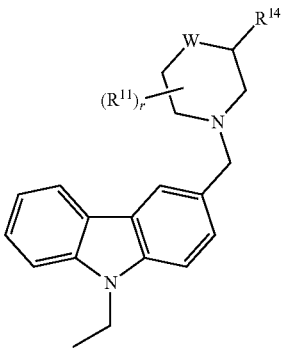

or a pharmaceutically acceptable salt, ester, or prodrug thereof, wherein

W is chosen from C, N, and O;

r is 0-3;

each $R^{11}$ is individually chosen from hydrogen, halogen, hydroxy, lower hydroxyalkyl, lower alkyl, halogen, lower haloalkyl, lower alkoxy, lower haloalkoxy, monocyclic 5-membered heteroaryl, $C(O)OR^{12}$, $C(O)N(R^{12})(R^{13})$, perfluoromethyl, and perfluoromethoxy;

$R^{12}$ and $R^{13}$ are individually chosen from hydrogen, lower alkyl, lower cycloalkyl, lower cycloalkylalkyl, lower heterocycloalkyl, lower heterocycloalkylalkyl, lower heteroaryl, lower heteroarylalkyl, any of which may be optionally substituted with one or more substituents chosen from halogen, hydroxy, cyano, lower alkyl, lower alkenyl, lower alkynyl, lower heteroalkyl, lower alkoxy, lower haloalkyl, and lower haloalkoxy; and $R^{14}$ is an unsubstituted five-membered monocyclic heteroaryl.

4. The compound as recited in claim 3 wherein $R^{12}$ and $R^{13}$ are individually chosen from hydrogen and lower alkyl.

5. The compound as recited in claim 4, wherein $R^{11}$ is chosen from hydrogen, lower alkyl, and monocyclic 5-membered heteroaryl.

6. The compound as recited in claim 5, wherein $R^{11}$ is monocyclic 5-membered heteroaryl.

7. The compound as recited in claim 6, wherein r is 0 or 1.

8. The compound as recited in claim 7, wherein said monocyclic 5-membered heteroaryl contains nitrogen and carbon atoms only.

9. A compound chosen from
3-((3-(1H-pyrazol-5-yl)piperidin-1-yl)methyl)-9-ethyl-9H-carbazole,
3-((3-(1H-tetrazol-5-yl)piperidin-1-yl)methyl)-9-ethyl-9H-carbazole,
3-((3-(1H-imidazol-2-yl)piperidin-1-yl)methyl)-9-ethyl-9H-carbazole,
3-((3-(1H-1,2,3-triazol-1-yl)piperidin-1-yl)methyl)-9-ethyl-9H-carbazole,
3-((3-(4H-1,2,4-triazol-3-yl)piperidin-1-yl)methyl)-9-ethyl-9H-carbazole,
3-((3-(1H-Imidazol-5-yl)piperidin-1-yl)methyl)-9-ethyl-9H-carbazole,
3-((3-(1H-1,2,3-triazol-5-yl)piperidin-1-yl)methyl)-9-ethyl-9H-carbazole, and
3-((3-(1H-pyrazol-4-yl)piperidin-1-yl)methyl)-9-ethyl-9H-carbazole.

10. A pharmaceutical composition comprising a compound as recited in claim 1, together with a pharmaceutically acceptable carrier.

* * * * *